(12) United States Patent
Haider et al.

(10) Patent No.: US 9,714,900 B2
(45) Date of Patent: Jul. 25, 2017

(54) METHOD AND APPARATUS FOR SELECTING WAVELENGTHS FOR OPTICAL MEASUREMENTS OF A PROPERTY OF A MOLECULAR ANALYTE

(71) Applicant: Mayo Foundation for Medical Education and Research, Rochester, MN (US)

(72) Inventors: Clifton R. Haider, Rochester, MN (US); Barry K. Gilbert, Rochester, MN (US); Gary S. Delp, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/397,810

(22) PCT Filed: Apr. 29, 2013

(86) PCT No.: PCT/US2013/038621
§ 371 (c)(1),
(2) Date: Oct. 29, 2014

(87) PCT Pub. No.: WO2013/165887
PCT Pub. Date: Nov. 7, 2013

(65) Prior Publication Data
US 2015/0119661 A1      Apr. 30, 2015

Related U.S. Application Data

(60) Provisional application No. 61/640,682, filed on Apr. 30, 2012, provisional application No. 61/789,565, filed on Mar. 15, 2013.

(51) Int. Cl.
*G01N 21/31* (2006.01)
*A61B 5/1455* (2006.01)
(Continued)

(52) U.S. Cl.
CPC ......... *G01N 21/314* (2013.01); *A61B 5/0075* (2013.01); *A61B 5/1455* (2013.01);
(Continued)

(58) Field of Classification Search
None
See application file for complete search history.

(56) References Cited

U.S. PATENT DOCUMENTS 5,857,462 A * 1/1999 Thomas ............. A61B 5/14532
600/310
2002/0094531 A1* 7/2002 Zenhausern ........... C12Q 1/686
435/6.11
(Continued)

*Primary Examiner* — Shawn Decenzo
(74) *Attorney, Agent, or Firm* — Yakov Sidorin; Quarles & Brady LLP

(57) ABSTRACT

A system and optimization algorithm for determining the preferred operational wavelengths of a device configured for measurement of molecular analytes in a sample. Operational wavelengths are determined by solving a system of equations linking empirically defined functions representative of these analytes, spectrally dependent coefficients corresponding to these analytes, path lengths traversed by waves probing the analytes at wavelengths corresponding to the absorption level described by the functions representative of these analytes, and, optionally, a cost-function taking into account at least one of spectral separation between the operational wavelengths, manufacturability of wave source(s) producing wave(s) at operational wavelength(s), and the noise factor associated with the operation of such wave source(s).

30 Claims, 10 Drawing Sheets

(51) Int. Cl.
  *G01N 21/27*    (2006.01)
  *G01N 33/49*    (2006.01)
  *G01N 21/47*    (2006.01)
  *G01N 21/49*    (2006.01)
  *A61B 5/00*     (2006.01)
  *A61B 5/145*    (2006.01)
  *G01J 3/10*     (2006.01)
  *A61B 5/1495*   (2006.01)
  *G01J 3/12*     (2006.01)
  *G01N 21/3504*  (2014.01)
  *G01N 21/21*    (2006.01)
  *G01N 21/64*    (2006.01)

(52) U.S. Cl.
  CPC ........ *A61B 5/1495* (2013.01); *A61B 5/14532* (2013.01); *A61B 5/14539* (2013.01); *A61B 5/14546* (2013.01); *A61B 5/14551* (2013.01); *G01J 3/10* (2013.01); *G01J 3/12* (2013.01); *G01N 21/274* (2013.01); *G01N 21/474* (2013.01); *G01N 21/49* (2013.01); *G01N 33/4925* (2013.01); *G01J 2003/104* (2013.01); *G01N 21/21* (2013.01); *G01N 21/3504* (2013.01); *G01N 21/64* (2013.01); *G01N 2021/3144* (2013.01); *G01N 2201/06113* (2013.01)

(56) References Cited

U.S. PATENT DOCUMENTS

2007/0135694 A1* 6/2007 Sato .................. A61B 5/14553
                                              600/328
2008/0312533 A1* 12/2008 Balberg ............. A61B 5/14546
                                              600/437

* cited by examiner

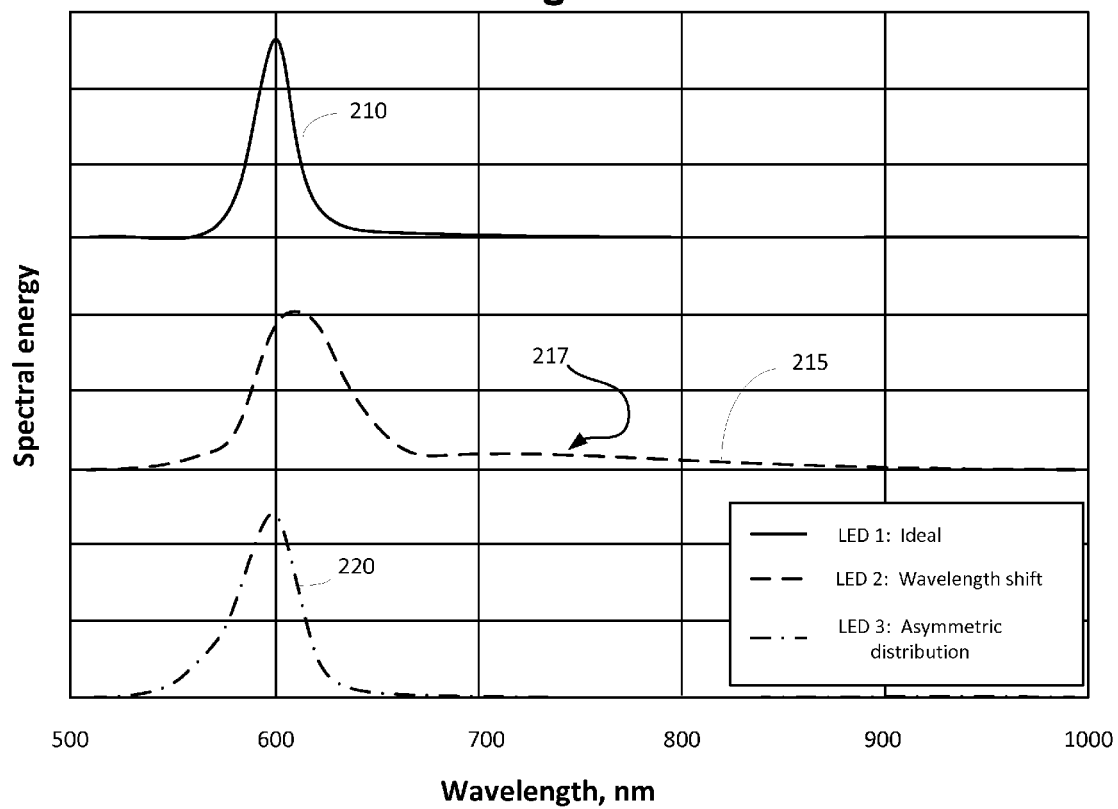

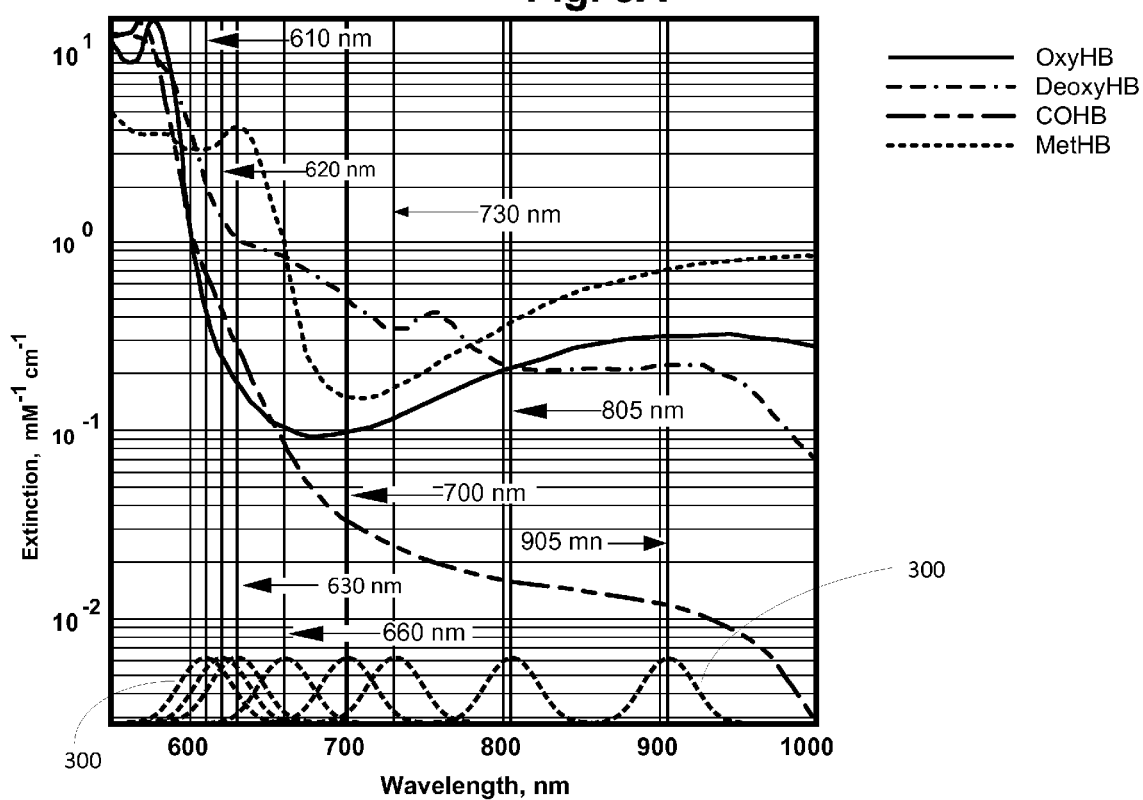

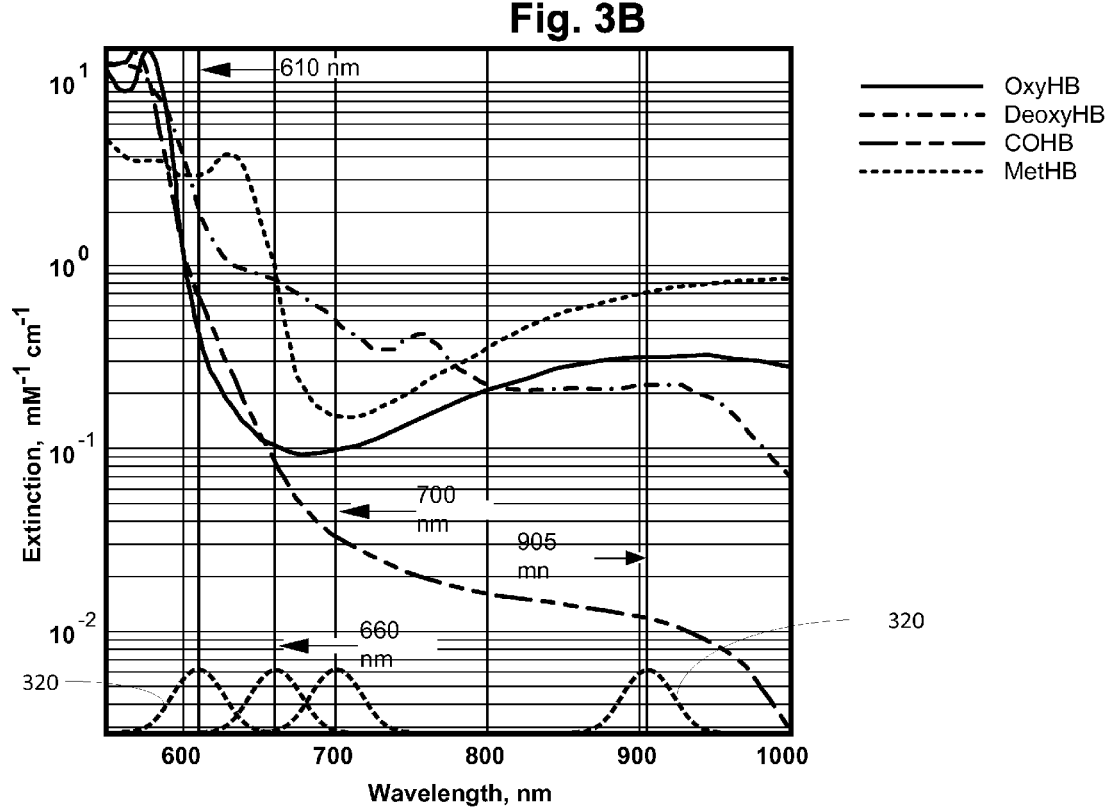

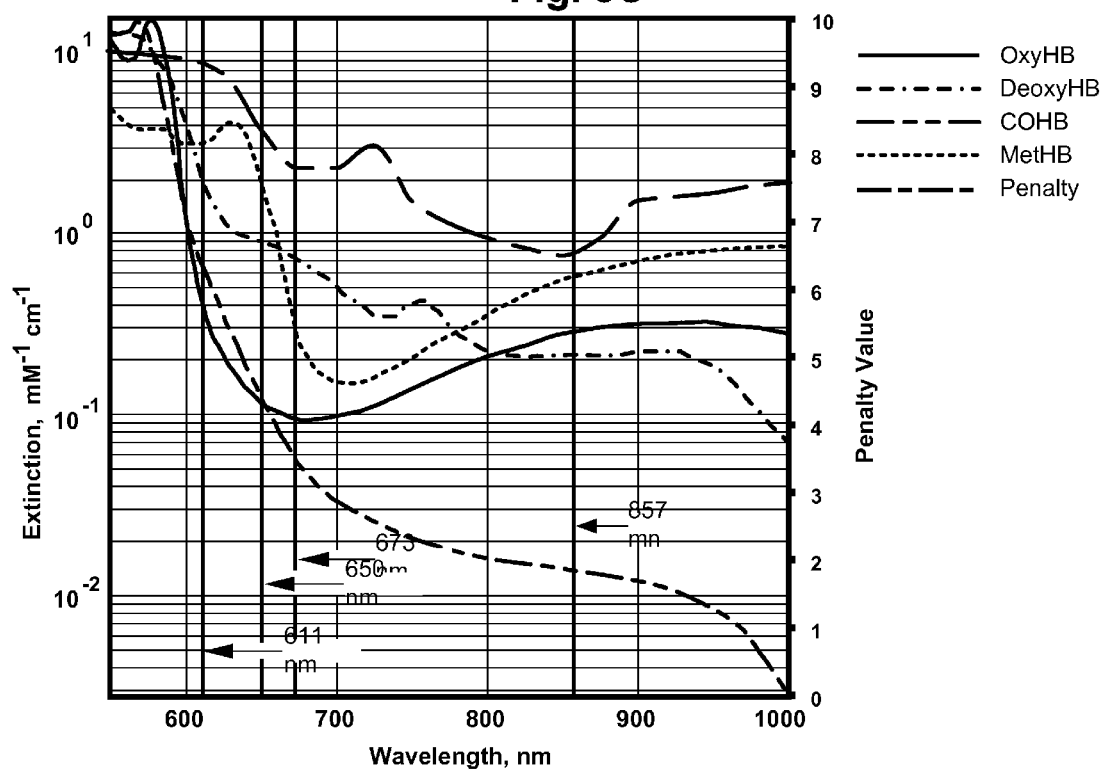

METHOD AND APPARATUS FOR SELECTING WAVELENGTHS FOR OPTICAL MEASUREMENTS OF A PROPERTY OF A MOLECULAR ANALYTE

CROSS-REFERENCE TO RELATED APPLICATIONS

This patent application is national stage entry of International Application No. PCT/US2013/038621 filed on Apr. 29, 2013, which claims benefit of and priority from the U.S. provisional patent applications Ser. Nos. 61/640,682 filed on Apr. 30 2012 and 61/789,565 filed on Mar. 15, 2013. Disclosure of each of the abovementioned patent applications is incorporated herein by reference in its entirety.

TECHNICAL FIELD

The present invention relates to spectroscopic systems and methods for selecting the operating wavelengths of a device configured to detect and/or measure spectrally dependent properties of material components of a sample, such as molecular analytes associated with the sample. In particular, the present invention relates to methods for optimal determination of optimal operational wavelengths for a VCSEL-based pulse oximeter.

BACKGROUND OF THE INVENTION

The assessment of arterial blood and tissue oxygen saturation has been shown to be critical for monitoring, diagnosing, and treating acute cardiovascular deficiencies, for example but not limited to low blood oxygen saturation due to chronic obstructive pulmonary disease (COPD) or, in extreme cases, exsanguinations. Further, the time line over which physiological changes occur is indicative of underlying cardiovascular deterioration. While techniques exist that allow qualitative monitoring of the level of arterial blood and tissue oxygen saturation, the current medical practice appears to lack a tool for quantitative monitoring of deteriorating cardiovascular status from the initial cardiovascular event or acute trauma through arrival at a medical facility.

Spectroscopy was originally the study of the interaction between radiation and matter as a function of wavelength ("$\lambda$"). Historically, spectroscopy referred to the use of visible light dispersed according to its wavelength, e.g. by a prism.

Later the concept of spectroscopy was expanded greatly to comprise any measurement of a quantity as a function of either wavelength or frequency. Thus, it also can refer to a response to an alternating field or varying frequency ("$\nu$"). A further extension of the scope of the definition added energy ("E") as a variable, once the very close relationship "E"="h$\nu$" for photons was realized ("h" is Planck's constant). A plot or measurement of the response of a material or structure as a function of wavelength—or more commonly frequency—is referred to as a spectrum.

ISO Standard number 80601-2-61:2011 states, on page 34: "Current technology requires an adequate concentration of haemoglobin, a pulsatile change in blood flow, and light transmission through a tissue bed to approximate the in vivo haemoglobin oxygen saturation. PULSE OXIMETER EQUIPMENT is not typically capable of functioning effectively during cardiopulmonary bypass or at extreme low-flow states, and is not at present intended as a means for the measurement of blood flow or blood volume. Given these limitations, PULSE OXIMETER EQUIPMENT does not provide precise measurements of arterial haemoglobin saturation. The presently marketed in vivo PULSE OXIMETER EQUIPMENT is not a replacement for measurement of blood samples by in vitro optical oximeters. The values derived from pulse oximetry are not a measurement of blood or solid-tissue oxygen tension. Pulse oximetry provides no direct indication of oxygen delivery to tissue, or of tissue oxygen consumption."

Recent theoretical developments have pointed to the potential advantage of a spectroscopic device that uses multiple wavelengths of light to perform oximetry. Spectroscopic devices (including oximeters) using multiple well-chosen wavelengths have improved accuracy without requiring the use of extremely large devices. There remains a need for a method to accurately select the optimal multiple wavelengths to enable a device that can acquire and process data for use in quantitative cardiovascular measurements. The multiple selected wavelengths are also beneficial in devices used for quantifying other material components from the acquired results, and optimization of the process of accurately and completely distinguishing between or among the analytes (referred to herein as analyte contrast).

Furthermore, there remains a need for improved measurement devices configured to operate to measure relative and/or absolute concentrations of molecular analytes in a sample. Conventional models have ignored path length and especially wavelength-based variations in a path length of an electromagnetic wave traversing a sample being measured. Incorporating this information can increase the sensitivity and accuracy of the measurements, providing a wealth of derived property evaluations. Some of the material components that are quantified include molecular analytes. Non-limiting examples of these molecular analytes are cells, proteins, hemoglobin, glucose, lipids, chromophores, water, pH, and gases such as hyperpolarized gases, carbon dioxide, carbon monoxide, and oxygen. Due to short transit times of signals, and the rich information conveyed in the variations in the impulse and therefore the step response of a sample, the accurate and fine-grained measurement of the step response by a spectrometric system is difficult but valuable.

Given the capability to utilize the fine-grained information for more accurate measurements and assessments, there is a need for systems, methods, and apparatus that incorporate the ability to accurately measure very small signal levels and very short transit time thereby providing the details of the collective differential path lengths of the transmitted signals.

SUMMARY

Embodiments of the invention provide a method for determining a regime of operation of a spectrometric device configured to generate electromagnetic waves (EMWs), where the device is cooperated with a sample to measure a property of a material component of the sample. The method includes the steps of (i) receiving, at a user-input device, data representing empirically-defined spectrally-dependent characteristic of at least first and second material components of the sample; (ii) defining a first system of equations representing the empirically-defined spectrally dependent characteristic as functions of at least respectively corresponding concentrations of the at least first and second material components in the sample and spectrally-dependent paths of EMWs through the sample, where the EMWs respectively correspond to the at least first sand second material components; and (iii) defining a second system of equations including the first system of equations and additional equations employing at least one parameter representing operational utility of the device. The method further includes (iv) a step of solving the second system of equations to determine wavelengths of operation of the device such as to ensure that the figure of merit, representing operational cost of employing the device, is locally optimized at the wavelengths of operation.

The step of receiving may include receiving data representing one or more of an attenuation coefficient, a scattering coefficient, a coefficient of anisotropy, a fluorescence parameter, an index of refraction, and a parameter representing a quantum response of the at least first and second material components to impinging EMWs. In a specific case, the attenuation coefficients include first and second molar attenuation coefficients. Alternatively or in addition, the material components include one or more of molecular analytes, cells, protein, hemoglobin, glucose, lipids, chromophore, gas (such as at least one of hyperpolarized gas, carbon dioxide, carbon monoxide, and oxygen) and water. The step of receiving may optionally include receiving data that represent spectrally-dependent absorption properties of at least first and second material components of the sample. The step of receiving may optionally include receiving data representing spectral dependence of a chosen characteristic of at least first and second material components of a sample that contains blood, where at least one of the first and second material components including blood analyte. The step of defining a second system of equations includes defining a matrix equation including a matrix coefficient representing one or more of a cost of manufacture of the device that operates at a wavelength of operation, an error associated with determination of said paths of EMWs, and a figure of merit associated with operational noise of the device at said wavelength of operation.

The step of defining a first system of equations includes defining a first system of equations representing the empirically-defined spectrally dependent characteristic as a function of respectively-corresponding concentrations, wherein said concentrations include at least one of a cell count, a protein count, a hemoglobin level, a glucose level, a lipid level, percent of a chromophore in the sample; a gas concentration; a carbon dioxide concentration; an oxygen concentration; a percent water; and a pH level.

The step of defining a second system of equations includes defining a matrix equation including a matrix coefficient representing a figure of merit associated with operational noise of the device, which operational noise is calculated as a function of a change in absorption said operational noise is calculated as a function of the change in absorption of the at least first and second material components as a wavelength of thee EMWs is varied.

The step of solving includes optimizing the figure of merit that includes at least one of propagation of variance, a parameter representing manufacturing cost of the device, a parameter representing a size of the device, and a parameter representing power consumption of the device.

Alternatively or in addition, the step of solving includes, in a specific implementation, solving the second system of equations to determine first and second wavelengths of operation one of which is shorter that an isosbestic wavelength corresponding to said first and second material components and another is longer than said isosbestic wavelength. The step of solving includes employing an iterative algorithm comprising at least one of a simulated annealing algorithm, a gradient descent algorithm, and a linear programming algorithm.

Embodiments of the present invention further provide a spectrometric system for measuring a property of a sample. Such system includes a source of electromagnetic radiation (EMR) enabled to generate the EMR of at least one wavelength of operation from a set of pre-determined wavelengths of operation; and a detector of the EMR in operable communication with the at least one source. The system additionally includes a supporting structure adapted to juxtapose the source and the detector with the sample; and a data-processing unit cooperated with the source and the detector and configured to quantify EMR received by the detector from the source through the sample and to generate output data representing such quantification. The system further includes a data-output device operable to present the output data in a user-defined format, and where the set of pre-determined wavelengths of operation is defined, based on first data representing empirically-defined spectrally-dependent characteristic of at least first and second material components of the sample, by solving a system of equations expressing the empirically-defined spectrally dependent characteristic(s). Such system of equations expresses the empirically defined spectrally dependent characteristic(s) as functions of at least (i) respectively corresponding concentrations of the at least first and second material components in the sample, (ii) spectrally-dependent paths of EMR corresponding to the at least first and second material components of the sample and propagating through the sample, and (iii) at least one parameter representing operational utility of the spectrometric device. The set of pre-determined wavelengths of operation is such that a figure of merit (that represents operational cost of employing the spectrometric device) is at least locally optimized.

A system of the invention may include a pulse oximeter. Alternatively or in addition, the empirically-defined spectrally-dependent characteristic of the at least first and second material components of the sample includes a light absorption characteristic. The set of pre-determined wavelengths of operation is defined by solving a system of equations that includes equations representing the empirically-defined spectrally dependent characteristic as a function of respectively-corresponding concentrations of the at least first and second material components of the sample. Such concentrations include at least one of a cell count, a protein count, a hemoglobin level, a glucose level, a lipid level, percent of a chromophore in the sample, a gas concentration; a percent water, and a pH level. In a specific implementation, the gas concentration includes at least one of a carbon dioxide concentration and an oxygen concentration, and the at least first and second material components include hemoglobin.

BRIEF DESCRIPTION OF THE DRAWINGS

FIG. 2 is a graph illustrating the spectral energy distribution of three light emitting diodes (LEDs).

FIG. 3A is a graph illustrating a choice of eight operational wavelengths in a pulse oximeter of the related art employing LEDs.

FIG. 3B is a graph illustrating a smaller number (four) of operational wavelengths for oximeters of FIG. 1A and FIG. 1B that still provide for adequate operation. The reduction of the number of the operational wavelengths is achieved with the use of an algorithm of the present invention.

FIG. 3C is a graph illustrating an optimal choice of spectrally independent bandwidths of a light-based spectroscopic device, determined with an algorithm of the invention. In addition, the graph shows the "penalty" curve (the "cost" curve, or the "figure of merit" curve) representing operational cost of employing such spectroscopic device

DETAILED DESCRIPTION

Figure 1A:
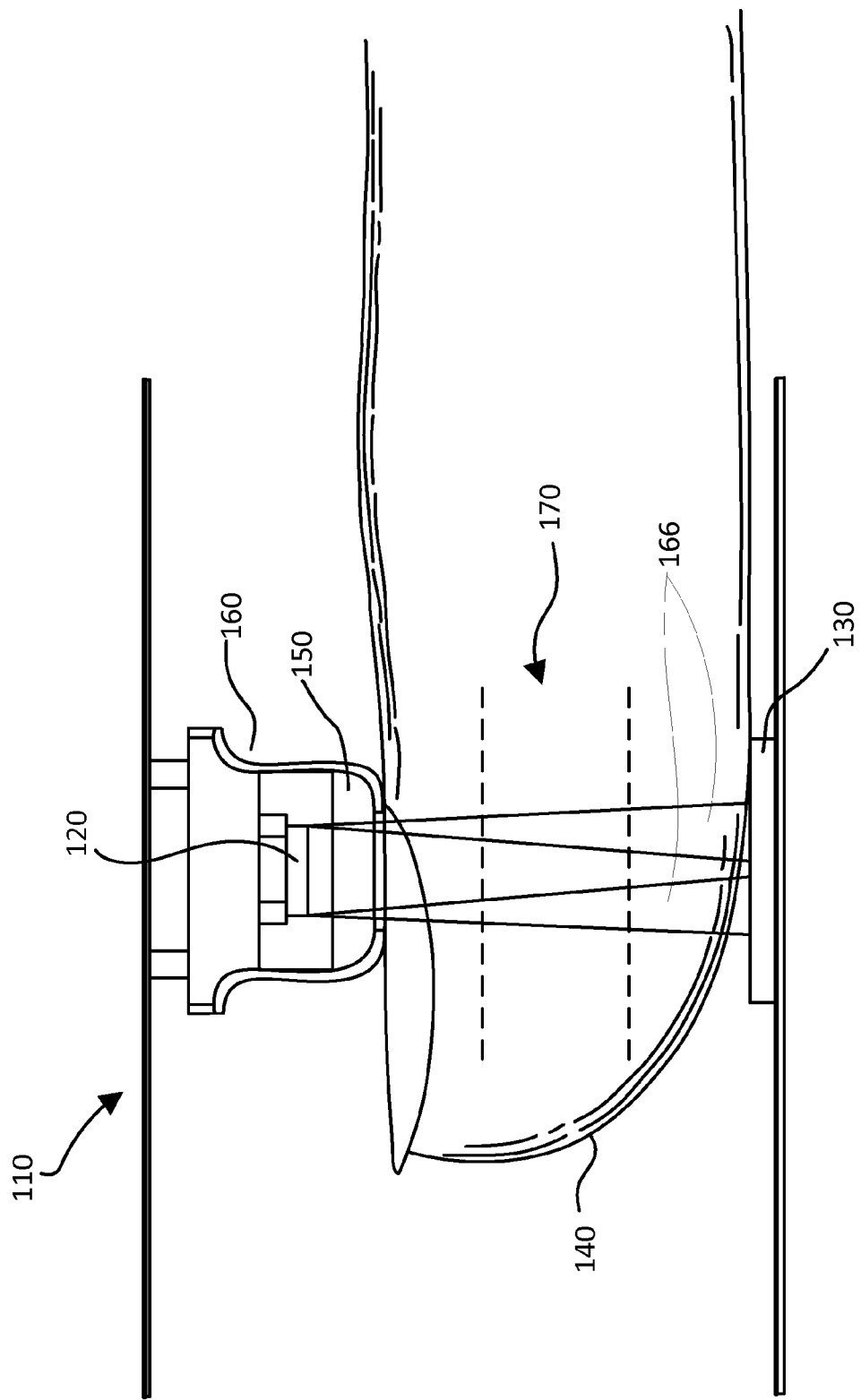
FIG. 1A is a diagram schematically illustrating an embodiment of a vertical cavity surface emitting laser (VCSEL) based oximeter.

References throughout this specification to "one embodiment," "an embodiment," "a related embodiment," or similar language mean that a particular feature, structure, or characteristic described in connection with the referred to "embodiment" is included in at least one embodiment of the present invention. No portion of this disclosure, taken on its own and/or in connection with a figure, is intended to provide a complete description of all features of the invention.

In the drawings, like numbers represent the same or similar elements wherever possible. No single drawing is intended to support a complete description of all features of the invention. In other words, a given drawing is generally descriptive of only some, and generally not all, features of the invention and may, for the purposes of simplification of the drawing, contain not all elements of a particular view or all features that can be presented. The invention may possibly be practiced without one or more of the specific features of the invention. Although a particular detail of an embodiment may not be necessarily shown in each and every drawing describing such embodiment, the presence of this detail in the drawing may be implied unless the context of the description requires otherwise. The described single features, structures, or characteristics of the invention may be combined in any suitable manner in one or more further embodiments.

Moreover, if the schematic flow chart diagram is included that illustrates the processing flow, the order in which processing steps or particular methods occur may or may not strictly adhere to the order of the corresponding steps shown.

The invention as recited in claims or clauses appended to this disclosure is intended to be assessed in light of the disclosure as a whole. While the invention may be described in reference to examples of an oximeter device, it is understood that, in general the scope of the invention covers, generally, a device generating and optionally detecting electromagnetic radiation.

The assessment of arterial blood and tissue oxygen saturation has been shown to be critical for monitoring, diagnosing, and treating acute cardiovascular deficiencies, such as chronic obstructive pulmonary disease (COPD), or in an extreme cases exsanguinations, for example. Further, the time line over which physiological changes occur is indicative of underlying cardiovascular deterioration. While techniques exist that allow for qualitative monitoring of the level of arterial blood and tissue oxygen saturation, the current medical practice appears to lack a tool for quantitative monitoring of deteriorating cardiovascular status from the initial cardiovascular event or physical trauma through arrival at a medical facility. Recent theoretical developments have pointed to the potential advantage of multi-wavelength oximeters, as a way to improve accuracy without extremely large devices. In addition to shortcomings of the commercially available multi-wavelength techniques described above, the determination of wavelengths at which the commercial oximeters operate is somewhat arbitrary and, as proven by practical use, results in the mixing of spectral data acquired from the patient. As a result, the data processing and retrieval of vital information is unnecessarily complicated. Currently used methodologies are therefore quantitatively suboptimal.

Pulse oximetry is generally used to continuously monitor the arterial blood oxygen saturation of the patient. The "pulse" comes from the time-varying amount of arterial blood in the tissue during the cardiac cycle. Typical pulse oximetry sensors employ a photodetector and a light source producing light at two or more wavelengths to measure the light that scatters and/or is transmitted through blood-perfused tissues. Wavelength selection traditionally emphasizes sensitivity to changes in arterial oxygen saturation ($SaO_2$, $SpO_2$), with at least one of the emitted wavelengths chosen to fall within the spectral region where the absorption coefficient of oxygenated hemoglobin (i.e., $O_2Hb$), is markedly different from that of deoxygenated hemoglobin (i.e., HHb). One example of a choice commonly practiced for the multiple sources of light for pulse oximetry is to use two light-emitting diodes (LEDs), one generating light with a spectrum centered at about 660 nm and the second LED generating light with a spectrum centered at about 900 nm.

It is also possible to measure other analytes in the arterial blood, such as dyshemoglobins (i.e., MetHb and COHb), with at least one additional wavelength for each analyte.

Oximeters may employ vertical cavity surface emitting lasers (VCSELs). The beam of light emanating from a traditional edge-emitting (also known as in-plane) laser device is usually elliptical in cross section and is often astigmatic. The angle of divergence of a beam from an edge-emitting laser is significant (on the order of 30 degrees by 10 degrees) thereby reducing the efficiency of coupling into an optical fiber. In contrast, a VCSEL device uses a shaped aperture to provide a more constrained light path, which results in a beam of circular cross section and of sufficient diameter to make the beam generally less divergent, typically at about a 10 degree angle. Operational characteristics of VCSELs are not discussed here in any more detail.

FIG. 1A illustrates schematically a probe module 110 in which the laser diodes are an integral part of the section of the probe. The probe module 110 contains one or more VCSELs 120, optionally spatially configured in a predetermined pattern or array. Each of the present VCSELs 120 generates a beam of light substantially centered at a selected wavelength. The probe module 110 also contains a light detector 130 configured to receive and detect light emitted by the laser diode(s) 120. The light detector 130 may include at least one of any suitable detector component, such as a photomultiplier tube (PMT), an avalanche photodiode, and a PIN diode, for example, and in a specific case may include an array of such detectors. The probe module 110 also contains a connector (not shown) adapted to operably cooperate the probe module 110 with a cable (not shown) that interconnects the probe with a monitor (not shown). The probe module 110 is shown to be juxtaposed to the patient's perfused tissue 140 (shown as a finger, for illustration purposes only). The probe module 110 is adapted to operate in the transmission mode (with the array of laser diodes 120 on one side of the finger 140 and the light detector 130 on the other side of finger 140). Alternatively, the probe may be adapted to operate in the reflectance or backscatter mode (where the elements 120 and 130 are positioned on the same side of the perfused tissue 140). The array of laser diodes 120 may include a diffuser 150 held in place by a mount 160. The diffusion of the light output is to ensure that light portion 166 generated by the array of laser diode light emitting devices 120 is not spatially concentrated and cannot cause harmful effects if mistakenly redirected to the patient's eyes. The change in the path length of the light portions 166 as they pass through the arteriolar bed 170 is a figure of merit used for determination of the concentration of blood analytes. The close spacing of the laser diodes in the array 120 results in the plurality of light beams produced by the laser diodes traversing substantially a common path through the arteriolar bed 170, which improves the accuracy of the measurements.

Figure 1B:
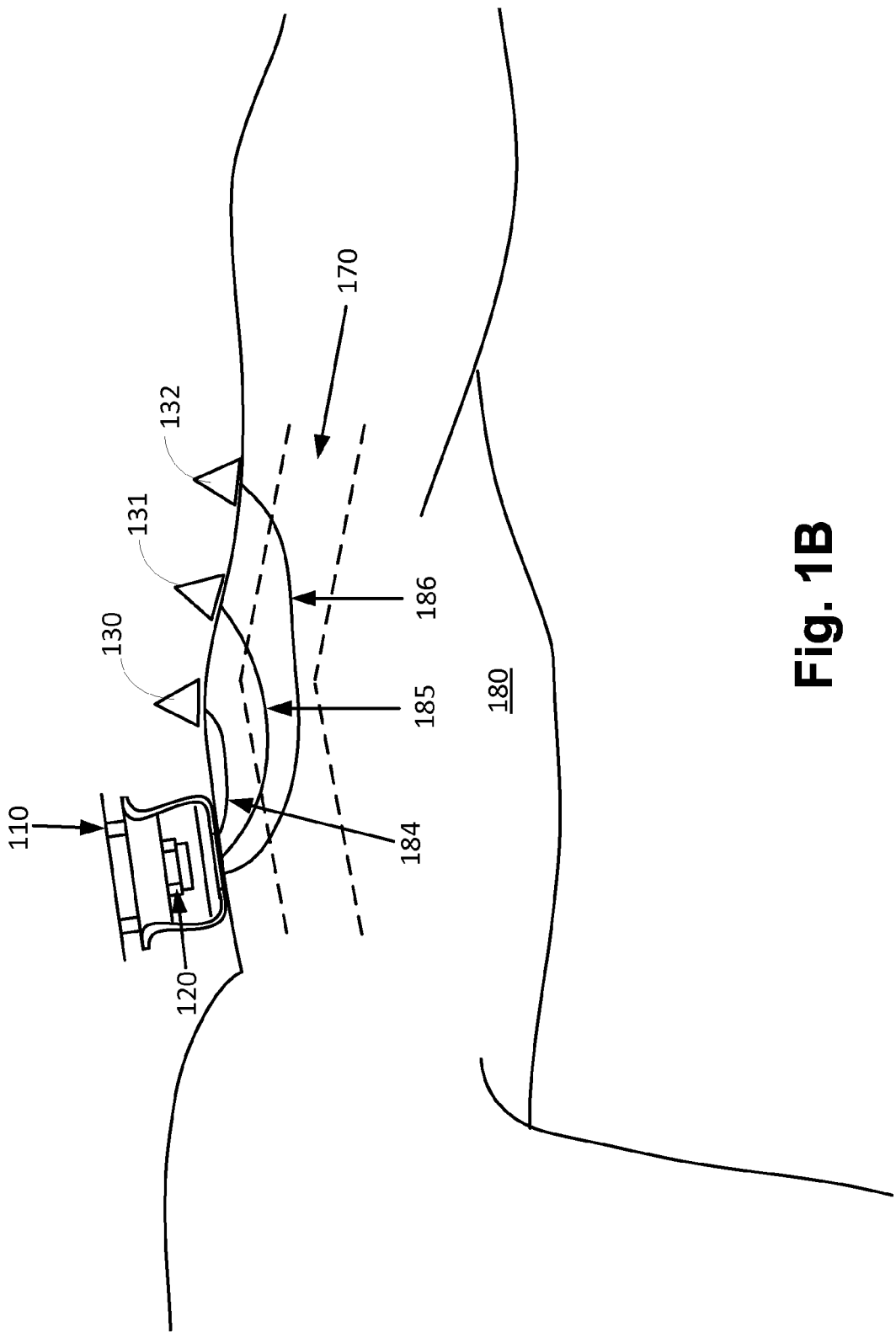
FIG. 1B is a diagram schematically illustrating an alternate embodiment of a VCSEL-based oximeter.

Referring to FIG. 1B, the probe module 110 is juxtaposed to the patient's tissue 170 (shown as an upper arm 180, as an example only) and multiple light detectors 130 are arranged in a predetermined geometry (e.g., array (square or rectangular), triangular, and pentagon) along the same surface of the upper arm 180. Optical paths 184, 185, and 186 determined by propagation of light from the light source 120 to the light detectors 130, 131, and 132 respectively, may traverse substantially different depths of the tissue 170 and, possibly, the arteriolar bed. The light detectors can generally be positioned at predetermined distances one from another. In this case, a pulse wave propagating through the tissue 170 is separately detectable by the spatially separated light detectors 130, 131, and 132. The time differences in the pulse-based analyte composition data associated with light received by these detectors is used to determine various characteristics of the status of the patient such as, for example, cardiac stroke volume and beat-to-beat variation of cardiac stroke volume. Body locations at which the probe is placed may differ, depending on the application.

It is appreciated that sources of monochromatic light are generally desirable for use as emitters in an oximeter to avoid overlap of the spectral distributions among the emitters and to provide precise coordination of the spectral bandwidth of a given emitter with respect to the hemoglobin extinction spectral distribution curves. In particular, the full-width half-maximum (FWHM) value of an LED bandwidth typically exceeds at least several tens of nanometers. In contrast, the FWHM of a VCSEL's bandwidth is approximately 1 nm. In addition, the LEDs are typically manufactured without tight quality control of the central wavelength of the corresponding bandwidth because conventional applications of these light sources are in display technologies, not in quantitative measurement systems requires an operation at predetermined wavelength(s).

As another example, the operational variations in central wavelengths, bandwidths, and shapes of spectral curves among LEDs that in other applications may be presumed to be substantially identical, in applications such as those described below may significantly differ. To this end, FIG. 2 shows an example of spectrum 210 of an idealized LED. The curve has a symmetrical bandwidth centered at 600 nm. A second curve 215 corresponds to measurements of a nominally 600-nm-centered spectrum of an LED as manufactured. The imperfections of the LED-fabrication process result in a red shift of the central wavelength of the spectral band of the curve 215 as compared to that of the idealized curve 210, and in addition, a visibly present spectral output above 700 nm. The tail end 217 of the spectral emission curve 215 can have a measurable effect on the received signal from the perfused tissue. The magnitude and extent of the tail 217 portion of the spectral emission curve 215 is difficult to predict, measure, and account for as compared to the signal output at the nominal central wavelength. Yet another spectral curve 220 corresponding to a third LED, the spectrum of which is nominally centered at a 600 nm wavelength illustrates asymmetry of the spectral output with respect to the corresponding central wavelength. In contradistinction to LEDs, VCSELs can be manufactured with predictable and repeatable spectral outputs, both in terms of central wavelengths and bandwidths.

Another complicating factor is that the LEDs are mounted in the probe module, and are juxtaposed to the patient's skin. The LEDs are therefore subject to significant temperature fluctuations during the operation of the probe module, which may cause changes in wavelength output by the LEDs. This effect can introduce a dynamic variation across the LED array and cause a measurable source of error. Finally, another source of error is the so-called "venous prefiltering," wherein the spectral outputs of the LEDs are unevenly and unpredictably attenuated across the span of generated wavelengths by the venous and non-pulsatile arterial components of the blood. Such attenuation of light is a function of the oxygen saturation of the blood and wavelength of the light, varies from subject to subject, is temporal in nature, and varies within a given patient and across patients. The arterial blood flow is highly variable in the extremities of a patient, where the pulse oximetry readings are taken. The difference in oxygen saturation between arterial and venous components of the blood can be from as little as less than one percent to greater than twenty-five percent. The greater the spectral bandwidth of the light source, the greater the potential error from this source of error. Sources of errors are inherent in the LEDs as well as in the method of placing the LEDs on the patient's appendage to perform readings.

Accordingly, selection of the multiple operating wavelengths, at which a source of light (or a combination of sources of light) of a pulse oximeter should operate, becomes of critical importance. To this end, FIG. 3A presents a graph showing spectral distribution curves for four blood analytes (oxyhemoglobin, OxyHb; deoxyhemoglobin, DeoxyHb; carboxyhemoglobin, COHb; and methemoglobin, MethHb) and schematic indication of eight wavelengths (610 nm, 620 nm, 630 m, 660 nm, 700 nm, 730 nm, 805 nm, and 905 nm) and eight spectral distributions (labeled, collectively, as 300) that respectively correspond to the eight LED sources employed in a commercially-available hospital oximetry system. It is appreciated that the significant spectral overlap of the LEDs' light outputs (presumably centered at 610 nm, 620 nm, 630 m, 660 nm, 700 nm, 730 nm, 805 nm, and 905 nm) results in spectral mixing of the acquired data and at best, merely contribute to signal averaging to reduce background noise. In fact, as established by the methods and algorithms discussed below, light beams at only four wavelengths chosen from the above-mentioned eight wavelengths are sufficient to acquire the practically-significant majority of data to identify and characterize multiple hemoglobin species. FIG. 3B illustrates such selection of the four spectral distributions 320 from the set 300 of FIG. 3A. Using data acquired with the use of several different light sources operating at different wavelengths allows the user to obtain a solution representing multiple biochemical species.

While specific examples describing embodiments of the invention are presented below with applications to optical spectroscopy and, more specifically, oximetry, quantitative oximetry, or pulse oximetry of blood samples, embodiments of the invention can be used with other media (for example, gas or fluid) to identify and/or measure different analytes (for example, molecules or proteins). Although the particular implementations of the algorithm of the invention are described using matrix equations, the use of continuous equations for determination of one or more analytes is also within the scope of the invention. Similarly, VCSEL(s) could be replaced with other sources of light such as, for example, edge emitting semiconductor lasers, or light emitting diodes. Moreover, embodiments of the invention can be practiced with the use of different waves, not necessarily optical waves, such as radio waves or acoustic waves, for example.

When the sample under test includes biological tissue and/or blood, the properties of the sample determined with light at wavelengths that have been selected according to an embodiment of the invention are various. These properties include, for example, concentration of a functional or dysfunctional hemoglobin; glucose; a lipid; a protein; a chromophore; a gas (such as percent of oxygen or carbon dioxide); water, and pH level. Other properties that may be measured include normal or abnormal cell count and normal or abnormal protein levels. The scope of the present invention is not limited to biological tissue or the limited properties listed. The scope of the invention also includes measuring relative levels and quantitative amounts of molecular analytes in general, as present in living as well as non-living samples.

An embodiment of the invention providing for derivative processing may also provide for example, one or more of blood oxygen saturation level, blood glucose level, blood protein level, blood lipid level, total body water, central blood volume, concentration of fluorescent biomolecules or dyes, respiratory tidal volume, cardiac stroke volume, and beat-to-beat variation of cardiac stroke volume. The sample-probing waves can be varied by including time-based variations of position, angle, intensity, phase, and wavelength of the wave-emitting source. The sample may also be modified, for example, by introducing a calibrated amount of carbon monoxide (CO) to provide quantitative measurements of one or more properties of the sample. The scope of the present invention also includes recording the measurements over time, such that the time varying nature of the concentrations can be determined. Properties derived from this collection of data include heart rate, heart rate variability, stoke volume, stoke volume variability, and similar properties.

Implementations of an algorithm according to the present invention facilitate not only optimal optical detection of various species of hemoglobin that are found in chemical equilibrium with oxygen-saturated hemoglobin (oxyhemoglobin), such as deoxyhemoglobin (the desaturated form of hemoglobin) as well as dysfunctional methemoglobin, sulfhemoglobin, and carboxyhemoglobin (the latter being related to exposure to high environmental levels of carbon monoxide), but also enablement of determination of the relative percentage of each species in blood at any given time. To this end, a set of curves representing spectral distributions of the extinction coefficients (further referred to as absorption curves) for the multiple species of hemoglobin such as those illustrated in FIG. 3A. Understandably, to resolve multiple species from the optically-acquired spectral data one has to solve a system of equations. As an example, in the case of four hemoglobin species, at least four independent equations are required. To derive these equations, at least four sets of coefficients are needed to incorporate at least four linearly independent optical measurements of the spectral characteristics of a blood sample, and therefore at least four different optical wavelengths are required. The optical wavelengths, at which meaningful hemoglobin measurements can be performed, are in the range of about 450 nm to about 1000 nm. FIG. 3C illustrates examples of the absorption curves for the species of hemoglobin (specifically, curves of spectral dependence of extinction coefficients) and identifies optical wavelengths (as shown, 611 nm, 650 nm, 673 nm, and 857 nm) that are optimal in terms of resolving the four identified hemoglobin species with the lowest noise-to-signal ratio (NSR) or, alternatively, the highest signal-to-noise ratio (SNR). It is appreciated that a choice of different absorption curves and associated wavelengths of operation for the spectrometric device will correspond to a different NSR.

Analysis of the absorption curves of four hemoglobin species (e.g., oxyhemoglobin, deoxyhemoglobin, methemoglobin, and sulfhemoglobin) shows that any given species may define a high absorption figure of merit at some narrow range of frequencies, and a much lower absorption figure of merit at a different narrow range of frequencies. In order to measure and solve for the relative or absolute quantity of all four hemoglobin species simultaneously, ideally one has to select four linearly independent equations with four unknown wavelength-variables. One method to optimize the selection of wavelengths is to make these equations as linearly independent of one another as possible in order to yield the lowest NSR for all four measurements. Therefore, the four optical wavelengths should be chosen such that the respectively corresponding absorption curves have amplitudes, at these wavelengths, that differ from one another as much as possible. The wavelengths should be chosen such that each interaction of electromagnetic radiation (EMR) or electromagnetic waves (EMWs) with the analyte be captured. If all components are transparent to the EMR or EMWs at a particular wavelength, then that EMR or EMWs have very little interaction with the sample. If any of the analytes are substantially opaque at a given wavelength, the signal level received by a detector will be difficult to measure. Improving the combination of linear independence and the interaction of the energy with the analyte is captured by improving the propagation of variance in the system of equations. This is examined below in detail (and, in particular, in reference to Eqs. (29-39)).

According to Ward Cheney and David Kincaid (*Numerical Mathematics & Computing*, 7th Ed., Brooks Cole; Apr. 27, 2012), for matrix operations it is possible to compute a "condition number" that provides a gauge of the transfer of error in the input to the output of the operation. A system with a condition number of 1 is said to be well conditioned, higher calculated condition numbers indicate progressively ill-conditioned systems in solving the system $Ax=b$. If the linear system is sensitive to perturbations in the elements of A, or to perturbations of the components of b, then this fact is reflected in A having a large condition number.

In FIG. 3A, the condition number of the eight-wavelength solution was calculated to be 30.5; in FIG. 3B, the condition number was 33.1; in FIG. 3C, with optimally chosen wavelengths, the condition number was calculated to be 19.8; the larger the condition number, the more ill-conditioned the system. Note that in FIG. 3B, the choice of wavelengths was constrained to the choice of wavelengths included in FIG. 3A. While the condition number is higher in FIG. 3B than in FIG. 3A, other figures of merit, including the propagation of error, are much improved. The condition number is used here to illustrate one potential figure of merit. Note that without the constraint of wavelength choice, the condition number of FIG. 3C is improved in comparison with that of either FIG. 3A or FIG. 3B.

According to the idea of the invention, selection of the operating wavelengths for VCSELS for use in a pulse oximeter or optical spectrometer is carried out by forming a merit (or cost) function based on a cost-function approach that is not limited to, for example, the condition of the mixing matrix or propagation of variance. Some of the constraint parameters of the cost-function may include wavelength-specific penalty coefficients according to (i) manufacturability of the VCSEL or other components; (ii) bandwidth or spectral extent of the light source output; (iii) a central wavelength about which the bandwidth is substantially centered; (iv) transition areas that result in rapidly changing accuracy with minor changes in operating center wavelength; (v) differential path length or the average path that light of different frequencies traverses in the medium (S); (vi) optical path length error derived from the statistical distribution of path lengths associated with, for example, physiologically relevant changes in the medium; and (vii) analyte absorption equations. According to an algorithm of the invention, the devised overall cost-function applies all of these constraints (and additional constraints that may be required) at the same time in order to optimize the process of defining the operational wavelengths for the pulse oximeter or, more generally, a spectroscope for measuring spectrally dependent properties of material components.

The "Manufacturability" constraint parameter defines how easily or likely a VCSEL that operates at a chosen wavelength may be manufactured. In calculating the overall cost-function, a weighting or scaling (as discussed below, for example in reference to Eq. (40)) is performed if the chosen wavelength falls outside of the manufacturability constraining limits.

The "Bandwidth" constraint parameter facilitates the simulation of hypothetical VCSELs or LEDs or even a white light source to account for variance in the desired bandwidth and to allow for the optional input of actual light source profiles in-order-to test effectiveness in separating sharp transition regions.

The "Central wavelength" constraint parameter facilitates testing the effects of manufacturing tolerances on the performance of a given light source. If a particular type of spectral distributions has a large variance in central wavelengths, this parameter can be included as a constraint to minimize the error in the solution as a function of manufactured center frequency versus the desired central frequency.

The "Transition areas" constraint parameter takes into account the realization that the selection of a wavelength may be such that, in the vicinity of that wavelength, an absorption curve associated with the operation of the oximeter is rapidly changing (thereby introducing variability into the processing of acquired data).

The "Differential Path Lengths" constraint parameter accounts for the wavelength dependency of optical scattering coefficients, meaning that the optical path length will be different for each light source. In traditional oximetry, the path lengths are assumed equal and as such are not part of the consideration. However, in cases characterized by low oxygen saturation the difference in optical path lengths can result in a poor estimation of oxygen saturation. Accordingly, the algorithm of the invention takes into account a difference in path lengths corresponding to optical data acquisition at different wavelengths.

The "Interaction" constraint parameter accounts for the wavelength dependency of differentially excessive transparency and differentially excessive opaqueness of a sample or a material component of the sample such that there is either minimal interaction of an EM wave with the sample (transparency), or minimal level of signal received by a detection unit (opaqueness).

A method to minimize error in the solution utilizes the proposed algorithm. Such method includes simulated annealing, gradient descent (also known as steepest descent), and linear programming. In addition or alternatively, constraints such as full forward and inverse models using a Monte-Carlo approach are optionally included into or, alternatively, removed from a method depending on the desired system optimization, thereby to create a comprehensive understanding of the measurement of physiological variables. For example, constraints or penalties corresponding to a particular analyte need not be included in an overall cost-function if that analyte is not present in the medium.

Accordingly, as shown in FIG. 3C, a curve labeled as "penalty" represents a particular subset of a cost function, a scaling factor incorporated into the algorithmic process according to the invention to optimize the determination of the wavelength choice. This "penalty" function represents, for example, a consideration that lasers (and, in particular, VCSELS) at some wavelengths are easier to manufacture than lasers at other wavelengths. The use of the "penalty" function, as discussed below, effectively modifies the algorithm by shifting the selection of optimal laser wavelengths to minimize the penalty function or penalty figure of merit. If the optimization algorithm is run without inclusion of the penalty curve, the optimization process arrives at optimal wavelengths that may be quite different from those chosen without consideration of the penalty curve. Because of, for example, new laser manufacturing approaches, the shape of the penalty curve may change, and results of a new optimization may be determined by exercising the algorithm with the updated/changed penalty curve. If a valid solution requires the use of a laser source the manufacture of which is particularly expensive, the algorithm selects the corresponding wavelength and a "cost" threshold determines that the solution is not feasible provided a given design budget. Additional considerations can be incorporated into the statement of the problem, including other elements beyond manufacturing constraints on the optical sources, for example, relative optical responsiveness at varying wavelengths of, or manufacturing constraints on, the selected photodetectors that comprise the optical receiver portion of the system.

The wavelength selection process used to separate two distinct elements of blood (species of hemoglobin, also referred to herein as chromophores) is generally based on an empirical observation that measurements at one or more wavelengths are required to spectrally separate one or more chromophores. This observation serves as a basis for ensuring the minimal spectral mixing of the measured optical signals representing absorption of probing light by the one or more chromophores. As the number of chromophores of interest increases, so does the minimum number of wavelengths required to solve the system of wavelength-dependent equations. It has previously been documented in the open scientific literature to be computationally intractable to define more than a couple of chromophores on a limited subset of the wavelengths of interest, making the solution suboptimal by definition. However, according to the idea of the invention, the algorithm for selection of wavelengths for an oximeter does provide an optimized solution (corresponding to laser sources operating at optimally-defined wavelengths or, alternatively, laser sources available commercially and operating at wavelengths that are close to those defined by an optimization algorithm) based at least on minimizing the pre-determined figure of merit. An example of the pre-determined figure of merit is provided by propagation of variance from the measurements to the solution. The algorithm may be used to locate near-optimal solutions, or constrained solutions, that use particular wavelengths fixed as part of the solution. This approach may be advantageously used when a given set of VCSELs at fixed wavelengths are commercially available, and new wavelengths are available only at a considerable incremental cost. The algorithm can additionally be used to identify an optimal set of wavelengths, which can then drive the process of specially designing and manufacturing VCSELs that operate at central wavelengths corresponding to the wavelengths from the optimal set.

Figure 3D:
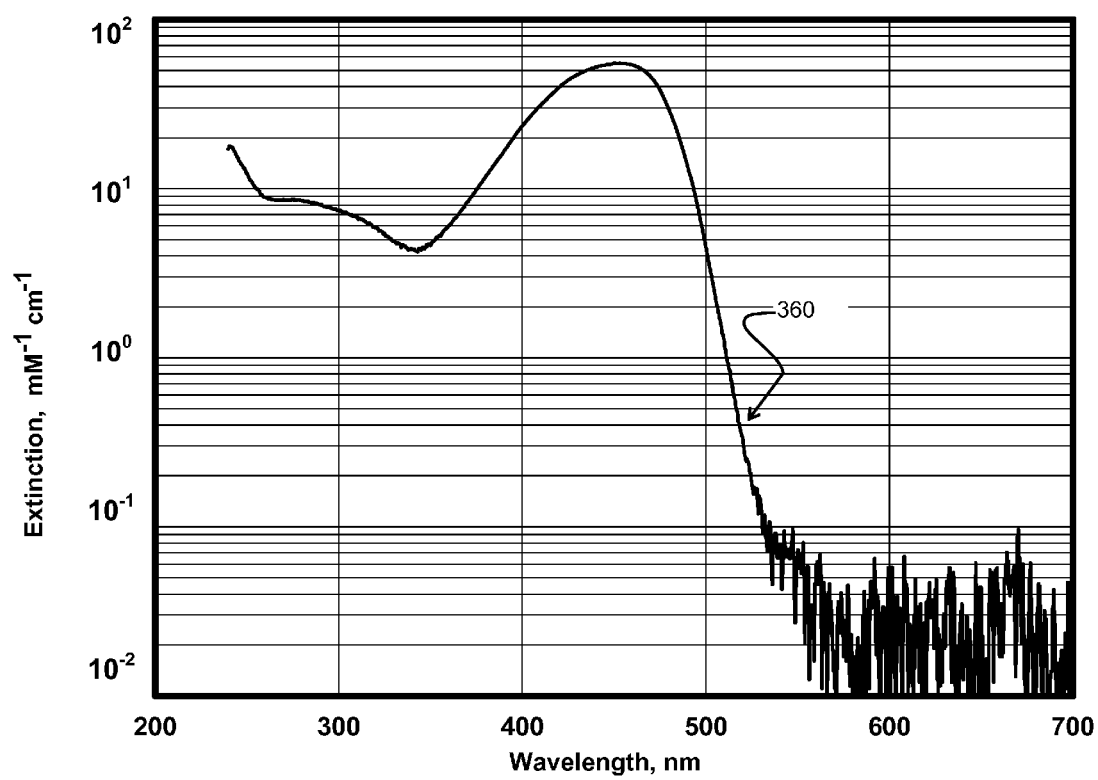
FIG. 3D is a graph illustrating the spectral distribution of the extinction coefficient characterizing Bilirubin (a possible confounding analyte) in chloroform.

When considering the choice of wavelengths at which the spectrometric device, used in a particular application, should preferably operate it is necessary to consider the material components of the sample to be measured. Some of these material components—referred to herein as potentially confounding components—are the material components of the sample the presence of which will affect the spectrum associated with the measurement(s) of the sample, the presence of which will affect at least one of the levels of the signal propagated through the sample, and the level of interaction of the signal with the sample. Such consideration requires the use of propagation of variance as opposed to the condition number. The curve 360 of FIG. 3D illustrates the optical extinction coefficients of Bilirubin in chloroform as they spectrally vary over the range from about 240 to about 700 nanometers. (Bilirubin is the yellow breakdown product of normal heme catabolism. Heme is found in hemoglobin, a principal component of red blood cells. Bilirubin is excreted in bile and urine.)

As can be empirically determined by the knee of the extinction curve 360 Bilirubin, as a material component of the measured medium, has greater extinction coefficients below 530 nm than above 530 nm. This characteristic illustrates some of the tradeoffs that are available with potentially confounding analytes. If the concentrations of the analytes are high enough to effect the measurements of the analytes of interest, then the error introduced by the range of potential concentration of the confounding analyte can be introduced as a spectrally-dependent cost of the measurement. This will lead the algorithms for determination of optimal wavelength(s) of operation of the spectroscopic device to choose wavelengths that are located in the spectral regions in which a given confounding analyte has little or no effect on the measurement. Alternatively, an additional wavelength (to account for a confounding material component of the sample) can be added to the algorithm, and the concentration of the confounding material component can be extracted from the other analyte determinations.

These two choices (providing a cost curve for interference, or adding the additional wavelength) are not mutually exclusive. It has been empirically found that if both are used as inputs to the algorithm when the additional wavelength is not needed, two of the wavelengths produced, as an output by the algorithm will be identical. Such optimization is a result of using propagation of variance as the figure of merit.

As was shown in the discussion of FIGS. 3A, 3B and 3C, a smaller number of wavelengths well chosen, based on the local optimization of a figure of merit representing operational cost of employing the device, improves the performance of the device.

Figure 4:
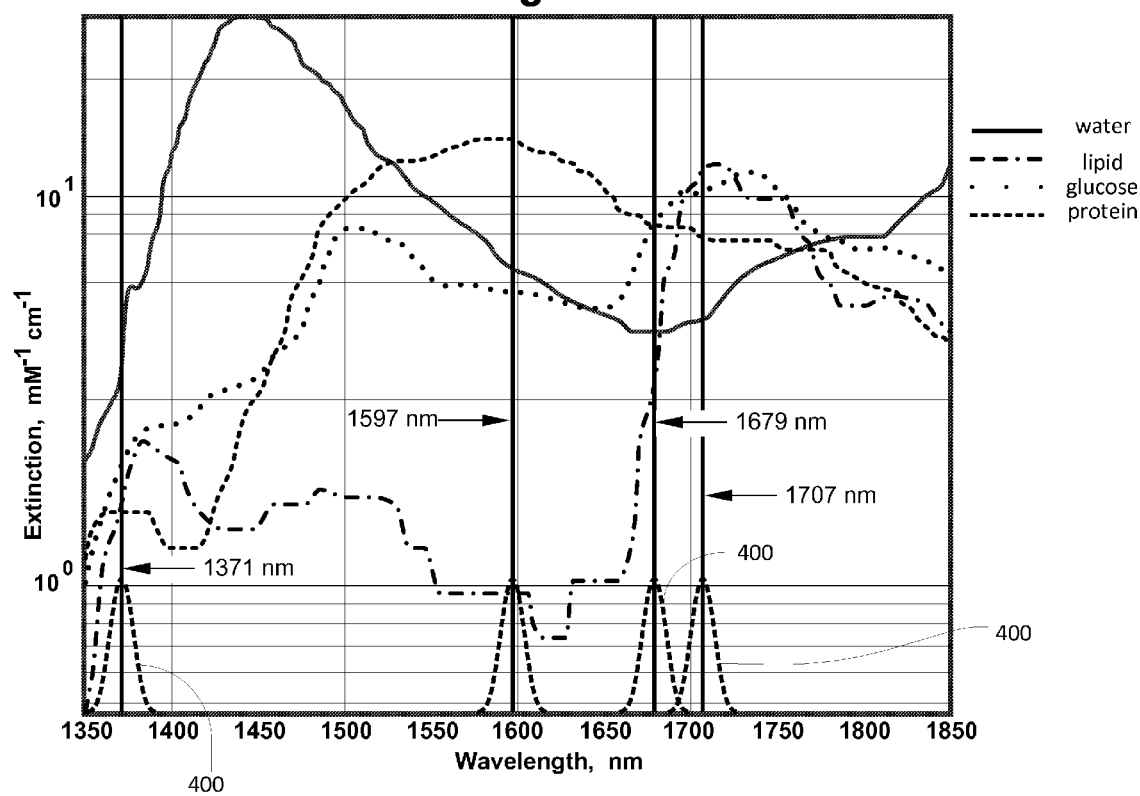
FIG. 4 is a graph illustrating an optimal choice of spectrally independent bandwidths of a light-based spectrographic measurement device, measuring glucose levels, determined with an algorithm of the invention

Optical noninvasive sensing methods facilitate detection of additional medically important, physiological and biochemical variables besides hemoglobin species. As one example, FIG. 4 offers a graph illustrating absorption curves for blood glucose, protein, and lipid in the near-IR range of 1350 nm to 1850 nm. The central wavelengths of spectral distributions 400 shown in this graph are longer than those in FIGS. 3A, 3B, and 3C because the differentiating extinction characteristics of the material components (that is, protein, lipid, and glucose) of interest exhibit themselves at longer wavelengths. An absorption curve for water is provided in FIG. 4 for comparison. It is expected, therefore, that given appropriate operating wavelengths, detection and measurements of glucose, lipids, normal and abnormal proteins, as well as natural analytes as well as manmade materials (for example certain chemical tags, markers, or dyes) in blood can be effectuated. In addition to the material components measured as shown in FIG. 4, other material components that can be measured include normal or abnormal cell counts. Finally, other concentrations such as percent of a chromophore, percent of a gas (such as oxygen or carbon dioxide), percent water, and pH level can also be measured. The above-mentioned material components are important as clinical parameters and in some cases as disease markers (for example, diabetes).

The solid vertical lines, marked with wavelength readings (such as 1371 nm, 1597 nm, 1679 nm, and 1707 nm) represent the central wavelength corresponding to four operating spectral distributions of light selected for detection of the above-mentioned species with the use of an optimization algorithm of the present invention. As the FWHM value for a VCSEL is on the order of one nm, the width of these vertical lines in the graph approximately represents the spectral distribution of VCSELs' light. The bell-shaped curves 400 (the peaks of which are substantially centered on the solid vertical lines), on the other hand, illustrate, in comparison, the broadband spectral distribution of LEDs that would be centered at the same wavelengths. The FWHM value for each LED is on the order of 50 to 100 nm or at least 50 times that of a VCSEL.

The use of these wavelengths, or a set of wavelengths determined to match the constraints described herein, that is an optimal or near optimal separation of the major molecular analytes, can be used as a non-invasive blood glucose level detector. The techniques described for multiple detectors 130 may be used.

Non-Scattering Absorbing Medium. As the light photons pass through a homogenous, lossy, nonscattering medium they are attenuated according to the attenuation coefficient $\mu_a(\lambda)$ of the bulk medium (BM) in relation to the traversed distance $\delta$, the irradiance of light changes in accordance with the Bouguer-Beer-Lambert exponential law, the probability of a photon being absorbed over a distance is $\Delta\delta$ is $\Delta\delta\mu_a(\lambda)$, and the mean free path between attenuating interactions $l_t(\lambda)$ is given by $l_t(\lambda_j)=\mu_a^{-1}(\lambda_j)$. As individual attenuating components or chromophores of the medium, denoted as are considered instead of the properties of a bulk medium, the properties of the bulk medium can be expressed as the summation of all N independent attenuating chromophores:

$$I(\lambda_j)=I_0(\lambda_j)\exp[-\Sigma_{i=1}^{N}\mu_a^{C_i}(\lambda_j)\delta^{C_i}]$$

Often $\mu_a(\lambda)$ is replaced with the molar extinction or molar attenuation coefficient $\epsilon(\lambda_j)$ [M$^{-1}$m$^{-1}$] to more easily allow formulation of the transmission of light as a function of concentration of the individual attenuating components [C$_i$] that comprise the nonscattering medium. For this substitution, for a given chromophore i, the attenuation A (in units of optical density, OD) and transmission coefficients T are related as $$A(\lambda_j) = \log_{10}\left(\frac{I_0(\lambda_j)}{I(\lambda_j)}\right) = \epsilon(\lambda_j, C_j)[C_i]\delta^{C_i} \qquad (2)$$

$$A(\lambda_j) = -\log_{10} T \qquad (3)$$
$$= -\log_{10}\left(\exp\left[-\sum_{i=1}^{N} \mu_a^{C_i}(\lambda_j)\delta^{C_i}\right]\right)$$
$$= \frac{\mu_a^{C_i}(\lambda_j)\delta^{C_i}}{\ln(10)}$$

Accordingly, $$\mu_a^{C_i}(\lambda_j) = \ln(10)\delta^{C_i}\epsilon(\lambda_j, C_j)[C_i] \qquad (4)$$

and $$A(\lambda_j) = \Sigma_{i=1}^{N}\delta^{C_i}\epsilon(\lambda_j, C_j)[C_i] \qquad (5)$$

If the optical density coefficient, A, is measured at multiple wavelengths, j=1 . . . M, it is expressed in vector and matrix notations as $$A = \Sigma_{j=1}^{M}\Sigma_{i=1}^{N}\delta^{C_i}\epsilon(\lambda_j, C_j)[C_i] \qquad (6)$$

and $$A = \epsilon[C]\delta \qquad (7).$$

Equation (7) can be re-written to account for bias G and noise N of the measurements, to result in $$A = \epsilon[C]\delta + G + N \qquad (8).$$

Given a known set of molar extinction coefficients, the measured values of optical density, and assuming that the non-scattering medium is homogeneous, the solution to Eq. (7) is provided by $$[C] = \epsilon^{-1}A(\epsilon^{CBM}) \qquad (9)$$

Scattering Non-Absorbing Medium. In a non-absorbing medium, light intensity is reduced along a ballistic path according to the scattering coefficient, $\mu_s(\lambda j)$ in relation to the distance $\delta$ traversed by the photons. The probability of a photon passing a distance $\Delta\delta$ without being scattered is $\Delta\delta\mu_s(\lambda_j)$ and, accordingly, $$I(\lambda_j) = I_0(\lambda_j)\exp[-\Sigma_{i=1}^{M}\mu_s^{C_i}(\lambda_j)\delta^{C_i}] \qquad (10)$$

The light scattering may be anisotropic, and the directionality of such scattering is described by the unitless factor g. With the use of a polar angle $\phi(0\leq\phi\leq\pi)$ and azimuthal angle $\psi(0\leq\psi\leq2\pi)$, g can be calculated as $$g = \frac{\int_{4\pi} p(\phi)\cos(\phi)\sin(\phi)\,d\phi d\psi}{\int_{4\pi} p(\phi)\sin(\phi)\,d\phi d\psi} \qquad (11)$$

where $p(\phi)$, which is the probability that a photon is scattered at an angle $\phi$ defined between the direction of incident light (the incident photon's unit vector) r and the scattered photon's unit vector r', is approximated by the Henyev-Greenstein function $$p(\phi) = \frac{1-g^2}{(1+g^2-2g\cos(\phi))^{\frac{3}{2}}} \qquad (12)$$
$$= \sum_{q=0}^{\infty} (2q+1)g^q P_q(\cos(\phi))$$

The scattering data can be acquired with the use of, for example, an integrating sphere and then correlated with the results of inverse Monte-Carlo simulations. When g=1, the light is considered to be completely forward-scattered, and when g=-1, the light is considered to be completely backward-scattered.

Scattering Absorbing Medium. To account for both scattering and absorbing properties of the medium, the total coefficient of interaction between a photon and the medium can be expressed as $$\mu_t(\lambda_j) = \mu_a(\lambda_j) + \mu_s(\lambda_j) \qquad (13)$$

The unitless albedo factor a is defined as $$a = \frac{\mu_a(\lambda_j)}{\mu_t(\lambda_j)} \qquad (14)$$

and the probability of scattering in such a medium is expressed as $$p(\phi) = a\frac{1-g^2}{(1+g^2-2g\cos(\phi))^{\frac{3}{2}}} \qquad (15)$$
$$= a\sum_{q=0}^{\infty} (2q+1)g^q P_q(\cos(\phi))$$

Anisotropy of light scattering in an absorbing medium is accounted for by introducing the reduced scattering coefficient $$\mu_s'(\lambda_1) = \mu_s(\lambda_j)(1-g) \qquad (16)$$

and the reduced total coefficient of interaction $$\mu_t'(\lambda_j) = \mu_a(\lambda_j) + \mu_s'(\lambda_j) \qquad (17)$$

It is conventionally recognized that, as g≥0, the likelihood of forward scattering increases, thereby decreasing the apparent attenuation of light along the path of travel. This conventional view does not take into account the information about a path that an individual photon of light has taken to reach a given point and only accounts for the total flux of light, i.e., $<\delta>\neq\delta$. Such a conventional approach, therefore, causes errors in the estimates of concentration. In particular, as $<\delta>>>\delta$, the concentration will be overestimated. Accordingly, the path length $\delta$ may be multiplied by a scalar constant to account for scattering and for the effective path of light $<\delta>$ that is not accounted for by the geometrical path of light $\delta$.

Scattering medium often defines the so-called diffusion regime where it is assumed that a steady-state fluence rate, $\Phi$, of light propagating away from a continuous-wave isotropic point light source of wavelength $\lambda_j$ can be modeled as a function of radius, $\Phi(r)$, in an infinite medium using the generic diffusion equation in which the effective attenuation coefficient, $\mu_{eff}$, is defined for the diffusion approximation:

$$\Phi(r) = \frac{3\mu'_s(\lambda_j)}{4\pi r} \exp(\mu_{eff}(\lambda_j)r). \tag{18}$$

Given these differences between the conventional model and the approach proposed here, it can be seen that information about the path length for an EM wave taken between transmitter and receiver is beneficial toward improving the accuracy of the derived properties measurements.

Oximetry: Considerations. The major chromophores of a blood sample include the functional hemoglobins oxyhemoglobin ($O_2Hb$) and deoxyhemoglobin (Hb), as well as the dysfunctional hemoglobins (i.e., dyshemoglobins or non-functional hemoglobins), carboxyhemoglobin (COHb), methemoglobin (MetHb), Glycosylated hemoglobin (GHb/Hb $A_{1c}$), and sulfhemoglobin (SulfHb). The total concentration of [Hb] is represented by [tHb], which is the summation of all the fractions according to $$[tHb]=[O_2Hb]+[Hb]+[COHb]+[MetHb]+[SulfHb]. \tag{21}$$

The summation of functional hemoglobin is given by $$[pHb]=[O_2Hb]+[Hb] \tag{22},$$

The oxygen saturation is determined as $$S_{O_2} = \frac{[O_2Hb]}{[pHb]}, \tag{23}$$

and the oxyhemoglobin fraction is determined as $$F_{O_2Hb} = \frac{[O_2Hb]}{[tHb]}. \tag{24}$$

Two-Wavelength Isosbestic Oximetry. If it is assumed that $O_2Hb$ and Hb are the only two functional hemoglobin species present in significant concentrations, then only two wavelengths are required to estimate $S_{O_2}$. The two wavelengths $\lambda_1$ and $\lambda_2$ can be chosen such that for $\lambda_1$ the corresponding $\epsilon(\lambda_1,O_2Hb)$ is maximally different from $\epsilon(\lambda_1,Hb)$, and such that $\lambda_2$ is an isosbestic point, i.e. that $\epsilon(\lambda_2,O_2Hb)$ exactly equals $\epsilon(\lambda_2,Hb)$. With that, the system of two linear equations requiring a solution is $$\begin{bmatrix} A(\lambda_1) \\ A(\lambda_2) \end{bmatrix} = \begin{bmatrix} \epsilon(\lambda_1, O_2Hb) & \epsilon(\lambda_1, Hb) \\ \epsilon(\lambda_2, O_2Hb) & \epsilon(\lambda_2, Hb) \end{bmatrix} \begin{bmatrix} [O_2Hb] \\ [Hb] \end{bmatrix} [\delta^{BM}] \tag{25}$$

It is assumed that the extinction coefficients are known and the attenuation (optical density) values have been determined empirically. Accordingly, the ratio of the optical density values at the two chosen wavelengths is $$\frac{A(\lambda_1)}{A(\lambda_2)} = \frac{\epsilon(\lambda_1, O_2Hb)[O_2Hb] - \epsilon(\lambda_1, Hb)[O_2Hb] + \epsilon(\lambda_1, Hb)[pHb]}{\epsilon(\lambda_2, O_2Hb)[pHb]} \tag{26}$$

and the oxygen saturation ratio is determined, therefore, from $$S_{O_2} = \frac{[O_2Hb]}{[pHb]} = \frac{\frac{A(\lambda_1)}{A(\lambda_2)}\epsilon(\lambda_2, O_2Hb) - \epsilon(\lambda_1, Hb)}{\epsilon(\lambda_1, O_2Hb) - \epsilon(\lambda_1, Hb)}. \tag{27}$$

Generalized Two-Wavelength Oximetry. The derivations provided above demonstrate a solution of the system of equations when an isosbestic point is chosen for one of the $\lambda$'s. Generally, one of the primary reasons behind using an isosbestic point is the simplification of such a solution to one that does not require a large amount of computational effort. Generally, however, if the above linear equations (25) are simply viewed as an unmixing matrix of two superimposed signals with known, unique mixing coefficients $\epsilon$, any $\lambda_1$ and $\lambda_2$ can be selected to estimate the oxygen saturation value—not necessarily the isosbestic wavelength points. Indeed, for two independent wavelengths $\lambda_1$ and $\lambda_2$ (or two non-overlapping spectral bandwidths respectively centered at $\lambda_1$ and $\lambda_2$), the Eq. (7) can be re-written as $$\begin{bmatrix} A(\lambda_1) \\ A(\lambda_2) \end{bmatrix} = \begin{bmatrix} 1.0 & 0.0 \\ 0.0 & 1.0 \end{bmatrix} \begin{bmatrix} [O_2Hb] \\ [Hb] \end{bmatrix} [\delta^{BM}]. \tag{28}$$

In this case, the coefficient matrix defines mixing $\epsilon$ factors that are mutually orthogonal and unitary. The corresponding noise amplification and propagation of variance are given as:
For noise amplification:

$$[g(\lambda_1),g(\lambda_2)]=\text{diag}[(\epsilon^H\Psi^{-1})^{-1}](\text{diag}[\epsilon^H\Psi\epsilon]) \tag{29a},$$

and $$[g(\lambda_1),g(\lambda_2)]=[1,1] \tag{29b}.$$

For propagation of variance:

$$[\sigma(\lambda_1),\sigma(\lambda_2)]=\sqrt{\Sigma[(\epsilon^H\epsilon)^{-1}(\Sigma^H)\text{var(Noise)}]} \tag{30a},$$

and $$[\sigma(\lambda_1),\sigma(\lambda_2)]=[1,1] \tag{30b}.$$

In contradistinction, for two spectral bandwidths that do overlap, a figure of merit needs to be defined, which takes into account such spectral mixing/overlap, in order to optimally select $\lambda_1$ and $\lambda_2$ and amplitude. According to an embodiment of the invention, the choice of two wavelengths for a spectrally overlapping case includes the determination of noise amplification and/or propagation of variance techniques. For example, with numerical coefficients chosen that are not linearly independent and therefore have a condition number greater than one and that result in mixing of the information, the solution becomes more complicated because $A(\lambda_1)$ now comprises signal components from $O_2Hb$ and Hb. Similarly $A(\lambda_2)$ now includes signal components from $O_2$ Hb and Hb; whereas $A(\lambda_1)$ should contain signal components solely from $O_2$ Hb, and $A(\lambda_2)$ should contain signal components solely from Hb. This contaminated or impure situation is thereby described as a mixing matrix or non-diagonal matrix. In the case of spectrally overlapping bandwidths corresponding to $$\begin{bmatrix} A(\lambda_1) \\ A(\lambda_2) \end{bmatrix} = \begin{bmatrix} 0.5 & 0.03 \\ 0.2 & 0.4 \end{bmatrix} \begin{bmatrix} [O_2Hb] \\ [Hb] \end{bmatrix} [\delta^{BM}], \tag{31}$$

the noise amplification is observed to increase as the mixing vectors become less orthogonal.

The propagation of variance equation should now account for the decreased orthogonality of the mixing vectors and the decreased ϵ-sensitivity, not otherwise predicted with noise amplification. In the propagation of variance, any decrease in ϵ sensitivity causes an independent decrease in SNR, because there is less interaction between light and the analyte for a given source-to-detector distance associated with the data acquired at each wavelength. However, ϵ, the interaction penalty, is not observed with noise amplification, and is a very important distinction between the two techniques. Because of this difference, noise amplification is the less preferred technique compared to the propagation of variance technique.

Here, for the above example, the interaction is demonstrated:

For noise amplification:

$$[g(\lambda_1), g(\lambda_2)] = \text{diag}[(\epsilon^H \Psi^{-1} \epsilon)^{-1}](\text{diag}[\epsilon^H \Psi \epsilon]) \quad (32a),$$

and $$[g(\lambda_1), g(\lambda_2)] = [1.1135, 1.1135] \quad (32b).$$

For propagation of variance:

$$[\sigma(\lambda_1), \sigma(\lambda_2)] = \sqrt{\Sigma[(\epsilon^H \epsilon)^{-1}(\epsilon^H)\text{var(Noise)}]} \quad (33a),$$

and $$[\sigma(\lambda_1), \sigma(\lambda_2)] = [2.0676, 2.7759] \quad (33b).$$

The above formulations do not account for the absolute wavelength-dependent E sensitivity and therefore a more general form of noise amplification and propagation of variance parameter may be needed; one skilled in the art can understand the additional constraints that apply for analytes. Unlike the noise amplification approach, the use of the propagation of variance technique for estimation of the oxygen saturation level $S_{O_2}$ depends on both the orthogonality of the ϵ sensitivities and the relative sensitivity of ϵ at each of the wavelengths. The optimal solution occurs when the signals are substantially not mixed spectrally (which corresponds to equation (28)), resulting in two independent equations and the relative ϵ sensitivities, each of which is equal to 1. This is important because noise amplification and propagation of variance techniques provide an unbiased estimate of the optimal $\lambda_j$'s that should be selected for a given set of chromophores in the experiment. One skilled in the art will observe that both of these approaches may be further adapted to the specific application.

Multiwavelength Oximetry. According to embodiments of the invention, the above-discussed methods are further extended to a case of multiwavelength oximetry (employing more than two operating wavelengths). Another approach may include a full-matrix solution of the equation such as equation (7) by analogy with that discussed in reference to equations (31, 32a, 32b, 33a, and 33b). It is appreciated that, with the increase of the number of operational wavelengths, the overall variance is increased as well. In the example shown below, five operational wavelengths $\lambda_1$ through $\lambda_5$ are used for determination of only two species (oxyhemoglobin and deoxyhemoglobin):

$$\begin{bmatrix} A(\lambda_1) \\ A(\lambda_2) \\ A(\lambda_3) \\ A(\lambda_4) \\ A(\lambda_5) \end{bmatrix} = \begin{bmatrix} 0.5 & 0.03 \\ 0.2 & 0.4 \\ 0.01 & 0.03 \\ 0.18 & 0.23 \\ 0.21 & 0.13 \end{bmatrix} \begin{bmatrix} [O_2Hb] \\ [Hb] \end{bmatrix} [\delta^{BM}]. \quad (34)$$

In this example, accordingly, for noise amplification:

$$[g(\lambda_1), g(\lambda_2)] = \text{diag}[(\epsilon^H \Psi^{-1} \epsilon)^{-1}](\text{diag}[\epsilon^H \Psi \epsilon]) \quad (35a)$$

and $$[g(\lambda_1), g(\lambda_2)] = [1.2155, 1.2155] \quad (35b).$$

For propagation of Variance:

$$[\sigma(\lambda_1), \sigma(\lambda_2)] = \sqrt{\Sigma[(\epsilon^H \epsilon)^{-1}(\Sigma^H)\text{var(Noise)}]} \quad (36a)$$

and $$[\sigma(\lambda_1), \sigma(\lambda_2)] = [1.8787, 2.5257] \quad (36b).$$

It is important that the wavelengths selected in multiwavelength oximetry be optimized to improve the orthogonality and analyte sensitivity of the mixing equation. Mere addition of supplementary wavelengths can have the effect of decreasing the SNR in the resulting estimate of $S_{O2}$. Further, according to the invention, selection of additional (supplementary) wavelengths is made dependent on the number of chromophores (elements of blood) to be measured. Specifically, the multiple wavelengths selected for determination of two chromophores (such as $O_2Hb$ and $Hb$, for example) may be different from the same number of multiple wavelengths selected for a five-chromophore oximetry measurement. The result of selecting multiple wavelengths according to the idea of the invention allows for the detection of dyshemoglobins, for example, and for improved sensitivity of the pulse oximeter or spectrometer device without adversely affecting the noise figure in the estimates of concentration of the functional hemoglobins. In one specific example:

$$\begin{bmatrix} A(\lambda_1) \\ A(\lambda_2) \\ A(\lambda_3) \\ A(\lambda_4) \\ A(\lambda_5) \end{bmatrix} = \begin{bmatrix} \epsilon(\lambda_1, C_1) \\ \epsilon(\lambda_2, C_2) \\ \epsilon(\lambda_3, C_3) \\ \epsilon(\lambda_4, C_4) \\ \epsilon(\lambda_5, C_5) \end{bmatrix} \begin{bmatrix} [O_2Hb] \\ [Hb] \\ [COHb] \\ [MetHb] \\ [rHb] \end{bmatrix} \begin{bmatrix} \delta^{C_1} \\ \delta^{C_2} \\ \delta^{C_3} \\ \delta^{C_4} \\ \delta^{C_5} \end{bmatrix}, \quad (37a)$$

where equation 37a is derived from equation 7 for the specific example using five exemplary material components ($O_2Hb$, $Hb$, $COHb$, $MetHb$, and $rHb$) of interest. Exemplary extinction coefficients are provided yielding:

$$\begin{bmatrix} A(\lambda_1) \\ A(\lambda_2) \\ A(\lambda_3) \\ A(\lambda_4) \\ A(\lambda_5) \end{bmatrix} = \begin{bmatrix} 0.50 & 0.03 & 0.01 & 0.01 & 0.01 \\ 0.20 & 0.4 & 0.01 & 0.01 & 0.01 \\ 0.01 & 0.04 & 0.40 & 0.07 & 0.01 \\ 0.18 & 0.23 & 0.01 & 0.60 & 0.01 \\ 0.21 & 0.13 & 0.01 & 0.07 & 0.40 \end{bmatrix} \begin{bmatrix} [O_2Hb] \\ [Hb] \\ [COHb] \\ [MetHb] \\ [rHb] \end{bmatrix} [\delta^{BM}], \quad (37b)$$

Similarly, as shown in equation 9, it is also desirable to be able to derive the concentration of the material components of interest given attenuations for each waveform transmitted. Using matrix operations on equation 37a, it is shown that the concentrations of each material component can be derived from the molar extinction coefficients $\epsilon(\lambda_i, C_i)$, attenuations $A(\lambda_i)$ of the waveforms, and the traversed distances $\delta^{C_i}$. This form of the equation is shown in equation 37c for using the distance associated with bulk media.

$$\begin{bmatrix} \epsilon(\lambda_1, C_1) \\ \epsilon(\lambda_2, C_2) \\ \epsilon(\lambda_3, C_3) \\ \epsilon(\lambda_4, C_4) \\ \epsilon(\lambda_5, C_5) \end{bmatrix} \begin{bmatrix} A(\lambda_1) \\ A(\lambda_2) \\ A(\lambda_3) \\ A(\lambda_4) \\ A(\lambda_5) \end{bmatrix} [\delta^{BM}]^{-1} = \begin{bmatrix} [O_2Hb] \\ [Hb] \\ [COHb] \\ [MetHb] \\ [rHb] \end{bmatrix}, \quad (37c)$$

equation 37d shows the same equation (37c) using the exemplary extinction coefficients shown previously in equation 37b.

$$\begin{bmatrix} 2.08 & -0.12 & -0.05 & -0.02 & -0.05 \\ -1.02 & 2.60 & -0.04 & -0.02 & -0.04 \\ 0.11 & -0.08 & 2.51 & -0.29 & -0.06 \\ -0.22 & -0.95 & -0.01 & 1.69 & -0.01 \\ -0.72 & -0.61 & -0.02 & 0.27 & 2.54 \end{bmatrix} \begin{bmatrix} A(\lambda_1) \\ A(\lambda_2) \\ A(\lambda_3) \\ A(\lambda_4) \\ A(\lambda_5) \end{bmatrix} [\delta^{BM}]^{-1} = \begin{bmatrix} [O_2Hb] \\ [Hb] \\ [COHb] \\ [MetHb] \\ [rHb] \end{bmatrix}, \quad (37d)$$

Referring to equation 37b, noise should also be taken into consideration. For noise amplification:

$$[g(\lambda_1), g(\lambda_2)] = \mathrm{diag}[(\epsilon^H \Psi^{-1} \epsilon)^{-1}](\mathrm{diag}[\epsilon^H \Psi \epsilon]) \quad (38a),$$

and $$[g(\lambda_1), g(\lambda_2)] = [1.3546, 1.3440] \quad (38b).$$

For propagation of variance:

$$[\sigma(\lambda_1), \sigma(\lambda_2)] = \sqrt{\Sigma[(\epsilon^H \epsilon)^{-1}(\epsilon^H)\mathrm{var(Noise)}]} \quad (39a)$$

and $$[\sigma(\lambda_1), \sigma(\lambda_2)] = [2.0936, 2.7927] \quad (39b).$$

Weight Function or Parameter. It is appreciated that, given the derivation of equation (7), additional wavelength-specific penalties or weighting factors can be incorporated via a two-dimensional (2D) or vector (1D) matrix W representing a cost-function that incorporates, for example, noise penalties. When the spectral channels of the oximeter (i.e., the operational wavelengths and associated spectral bandwidths) are independent (non-overlapping), W is the identity matrix $W_I$. Alternatively the $W=W_{sep}$ matrix can include penalties associated with the wavelength separation (which relates the separation to the increased difference in $\delta$ or the differential path length factor $<\delta>$ as the operational wavelengths are spaced further apart). In yet another implementation, an alternative or additional $W=W_{cost}$ weighting matrix can include penalties for the complexity or cost of manufacture of the source of light operating at a particular wavelength. Further, all or at least some of such weighting factors can be used in series to make the optimization of wavelength selection more practical. Accordingly, to incorporate a weighting function, the general matrix equation (7) can be re-written, for example, from $$[g(\lambda_1)W(\lambda_1), g(\lambda_2)W(\lambda_2)] \text{ and } [\sigma(\lambda_1)W(\lambda_1), \sigma(\lambda_2)W(\lambda_2)] \quad (40a)$$

to $$[g(\lambda_1)W_I W_{cost}(\lambda_1), g(\lambda_2)W_I W_{cost}(\lambda_2)] \quad (40b)$$

and $$[\sigma(\lambda_1)W_I W_{cost}(\lambda_1), \sigma(\lambda_2)W_I W_{cost}(\lambda_2)] \quad (40c)$$

Pulse Oximetry. According to one implementation of the invention, the oximetry data processing method that takes into account the "pulse" nature of the pulse oximetry data-acquisition (such as, for example, (i) the presence and/or parameters of the arterial pulse wave and (ii) the temporal point-spread function or impulse response associated with the tissue being measured, including the time-ordered sampling of the effect of the transfer function of the tissue on light passing through the object) determines the temporal dependence of light attenuation by the tissue. For example, in the case when the two chosen operational wavelengths/bandwidths do not overlap, the equation (7) may expanded to explicitly include the tissue and venous component factors:

$$\begin{bmatrix} A(\lambda_1, t) \\ A(\lambda_2, t) \end{bmatrix} = \quad (41)$$

$$\begin{bmatrix} \epsilon(\lambda_1, O_2Hb) & \epsilon(\lambda_1, Hb) & \epsilon(\lambda_2, \text{tissue}) \\ \epsilon(\lambda_2, O_2Hb) & \epsilon(\lambda_2, Hb) & \epsilon(\lambda_2, \text{tissue}) \end{bmatrix} \begin{bmatrix} [O_2Hb](t) \\ [Hb](t) \\ [\text{tissue}(t)] \end{bmatrix} \begin{bmatrix} \delta^{O_2Hb}(t) \\ \delta^{Hb}(t) \\ \delta^{\text{tissue}}(t) \end{bmatrix}.$$

In this example, and further considering the time-derivative of the equation (41) expressed as $$\frac{d[A(t)]}{dt} = \frac{d}{dt}\begin{bmatrix} A(\lambda_1, t) \\ A(\lambda_2, t) \end{bmatrix}, \quad (42)$$

the following assumptions are made:
(i) for a given chromophore, a portion of the absorption spectrum (of such a chromophore) that remains unchanged with time is set to zero by the above time derivative;
(ii) the effective distance traveled by light is substantially the same for all chromophores and equals $\Delta(\delta)$, or the change in distance caused by the arterial pulse, and
(iii) only two chromophores are being considered (which is an optional assumption specific only to this example).

The cancellation of the change in path length due to the arterial pulse-wave from the equation is achieved by, for example, defining a ratio of the equations (39) corresponding to two different wavelengths:

$$\frac{R_{\lambda_1}}{R_{\lambda_2}} = \frac{\frac{d[A(\lambda_1, t)]}{dt}}{\frac{d[A(\lambda_2, t)]}{dt}} = \frac{\epsilon(\lambda_1, O_2Hb)\Delta[O_2Hb] + \epsilon(\lambda_1, Hb)e[Hb]\Delta\langle\delta\rangle}{\epsilon(\lambda_2, O_2Hb)\Delta[O_2Hb] + \epsilon(\lambda_2, Hb)e[Hb]\Delta\langle\delta\rangle} \quad (43a)$$

$$\Delta[pHb] = \Delta[O_2Hb] + \Delta[Hb] \quad (43b)$$

The solution for the oxygen saturation level for pulse oximetry can be determined under these assumptions as $$S_{p,O_2} = \frac{\Delta[O_2Hb]}{\Delta[pHb]} = \quad (44)$$

$$\frac{\frac{R_{\lambda_1}}{R_{\lambda_2}}\epsilon(\lambda_2, Hb) - \epsilon(\lambda_1, Hb)}{\epsilon(\lambda_1, O_2Hb) - \epsilon(\lambda_1, Hb) + \frac{R_{\lambda_1}}{R_{\lambda_2}}(\epsilon(\lambda_2, Hb) - \epsilon(\lambda_2, O_2Hb))}$$

Given the similarity between the pulse oximetry solution (44) and the standard oximetry solution (27), one skilled in the art can appreciate that it is feasible that a wavelength selected to be optimal for standard oximetry may also be optimal for pulse oximetry.

Various embodiments of the disclosed methodology may be, at least in part, implemented in any conventional computer programming language. For example, some embodiments may be implemented in a procedural programming language (such as "C") or in an object-oriented programming language such as ("C++"). Other embodiments of the invention may be implemented as preprogrammed hardware elements (such as, for example, application specific integrated circuits, FPGAs, and digital signal processors).

Various embodiments of the inventions may be implemented as a system. A system for determining the preferred operational wavelengths of molecular-analytes measurement device(s) configured to measure molecular analytes in a sample includes a display device for displaying at least one feature associated with the sample and/or its spectral distribution of a physical characteristic describing such feature and/or data representing operation and availability of equipment used to characterize the sample. The system also includes a user-input device for selecting and modifying the feature or type of data at the display device.

The display device and the user-input device are in communication with a processor, which selects data representing the measurement device(s) from a measurement device(s) record set, such as operational constraint parameters and cost-functions described above. The processor further selects empirical data representing the sample from a corresponding record set corresponding to the at least one feature of the sample, such as an absorption curve corresponding to a chosen analyte. The record sets may be stored in a local database in operable communication with the processor or may be retrieved over a computer network from a remote database. Based on the determination of the chosen sample features and distribution of their spectral properties, and/or characteristics of measurement device(s), the processor creates edited data representing the modification of at least a portion of data retrieved from the record set(s), as well as a solution of a system of equations that link spectral distributions of the empirically-defined data representing the sample, path lengths traversed by interrogating waves (produced by the measurement device(s)) through the sample, as well as data representing the device(s).

The system further includes a digital memory that is in communication with the processor. The digital memory stores the associated edited data within an edit record set. The digital memory may be any of a random-access memory, a flash drive, a hard drive, or a disc drive, for example.

A system for displaying cartographic data includes an output display for presenting an output record set, which is also in communication with the processor. The processor retrieves edited data corresponding to the measurement of a chosen feature of the sample from the digital output record set, to create an output visual representation of same for the output display.

In an alternative embodiment, the disclosed system and algorithms may be implemented as a computer program product for use with a computer system. Such implementation includes a series of computer instructions fixed either on a tangible medium, such as a computer readable medium (for example, a diskette, CD-ROM, ROM, or fixed disk) or transmittable to a computer system, via an interface device (such as a communications adapter connected to a network over a medium). The medium may be a tangible medium (for example, optical, semiconductor, or analog communications lines). The series of computer instructions can embody all or part of the functionality previously described herein with respect to the system. Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software.

Examples of Algorithms for Solving Matrix Equations: Simulated Annealing. In one implementation, the technique referred to as simulated annealing is used to determine the optimum selection of wavelengths. Simulated annealing (SA) is a general meta-heuristic for locating a good approximation to the global optimum of a given function in a large search space. For the wavelength choice task, simulated annealing is more tractable than exhaustive enumeration. The name of the method comes from annealing in metallurgy, a technique involving heating and controlled cooling of a material to increase the size of its crystals and reduce their defects; both are attributes of the material that depend on its thermodynamic free energy. Heating and cooling the material affects both the temperature and the thermodynamic free energy. As illustrated in the flow diagram of FIG. 5, in this solution space, temperature is an analog for both the probable range of change selected in 'permute the solution' 510 between successive explorations of the solution space, and the likelihood P that that a "worse" solution will be chosen at 'evaluate choice' $P(E_{OLD}, E_{NEW}, Temp)$ 515. The analog for the thermodynamic free energy of metallurgy is the figure of merit $E_{WAVESET}$ used to evaluate the choice of wavelengths. Cooling is implemented in the Simulated Annealing algorithm as a slow decrease in the probability of accepting worse solutions as the algorithm explores the solution space. Accepting worse solutions is a fundamental property of this heuristic because it avoids the traps of locally optimal solutions that are worse than the global optimum.

Figure 5:
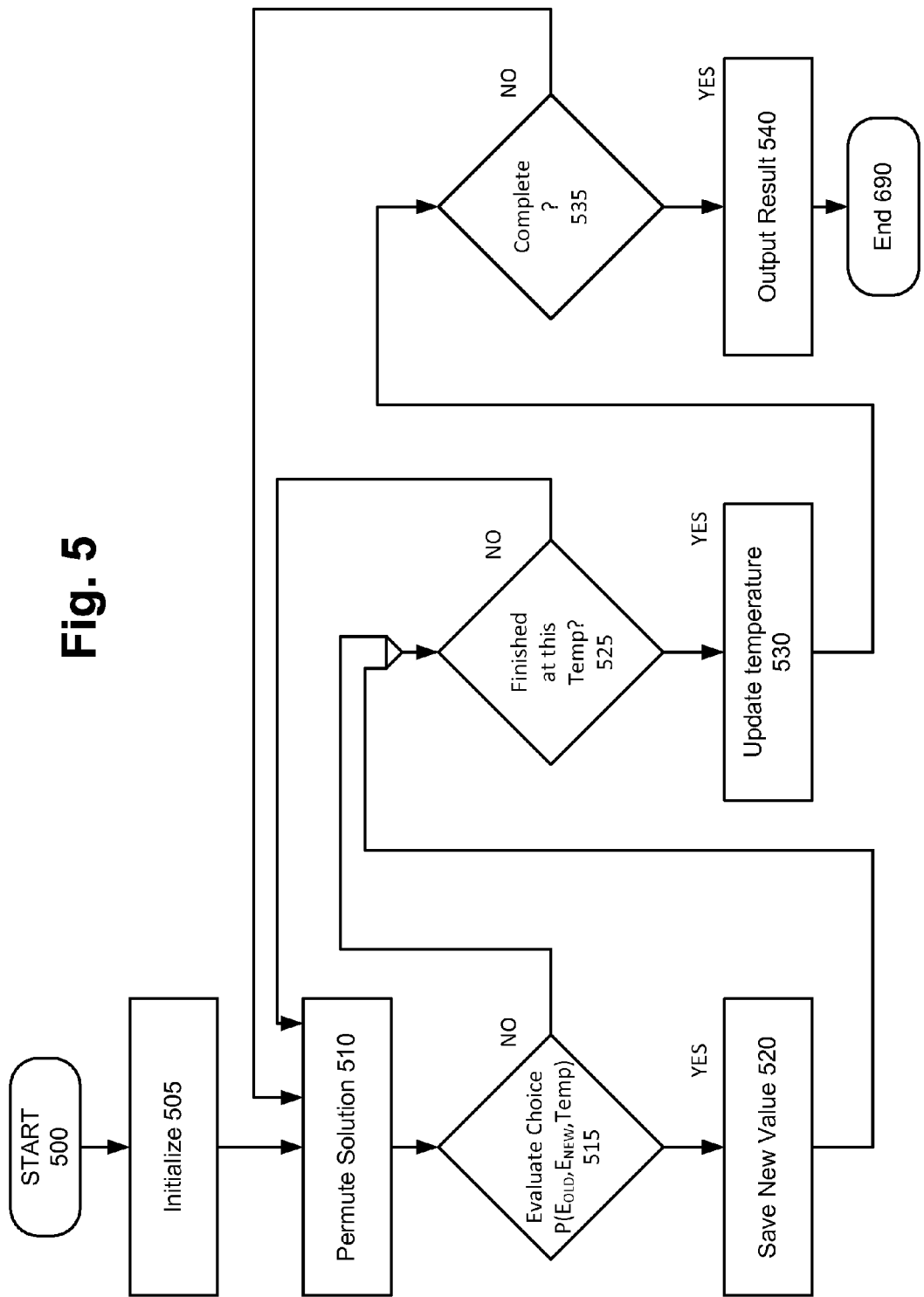
FIG. 5 is a flow chart illustrating an optimization algorithm defining a simulated annealing solution.

With reference to FIG. 5, a simulated annealing optimization algorithm initializes various data structures 505, including a starting point for the solution (selection of wavelengths), the equation to calculate the worthiness of the solution $E_{WAVESET}$ the present value of the goodness $E_{OLD}$ (referred to here as the energy of the solution, where energy is desired to be minimized), and a setting of the current "temperature" (Temp). Additional initialization may take place without loss of generality. The chosen solution is permuted (the selection of wavelengths is updated) at random from the possible solutions. The range of permutations is governed by the use of the "temperature" of the computation, said "temperature" to be reduced over the course of successive runs such that the range of possible solutions to be examined is updated in a stepwise fashion (for example, decreased) over time, as discussed below. As each permuted solution is evaluated, 515, if the objective function, $E_{WAVESET}$, yields a better number (which occurs if the "energy" of the permuted solution state is less than the previous state), then with probability $P(E_{OLD}, E_{NEW}, Temp)$ the present state is updated to reflect the permuted state, step 520. Proceeding from this step, it is evaluated if permutations at this energy level have completed. A number of techniques may be used for this evaluation, including but not limited to a count associated with a particular "temperature" step, or an evaluation of change over the last selected number of evaluation runs. If there are no more perturbations to be performed at this "temperature," the "temperature" is updated 530. If there are no more "temperature" selections to be performed, i.e., if the computation is complete 535, then the result is returned 540 and the algorithm finishes 545. If the evaluation 535 so determines, computation will continue at 510, producing an additional permutation at the new "temperature."

The properties of 'evaluate choice' $P(E_{OLD}, E_{NEW}, Temp)$ 515 are such that as the temperature (Temp) decreases, the likelihood of the lower of $E_{OLD}$ and $E_{NEW}$ will be chosen. As described above the objective function, $E_{WAVESET}(\lambda_1, \ldots, \lambda_N)$ is based on the wavelengths selected $(\lambda_1, \ldots, \lambda_N)$. Processing the wavelength choices through the spectrometric graphs determines the conversion matrix to be used from received signal to material composition. The matrix thus formed is evaluated for propagation of variance, and this result is weighted by the various cost functions related to the chosen wavelengths and the relation between the wavelengths. This operation produces the figure of merit for the particular choice of wavelengths. See Equations 40a-40c.

Figure 6:
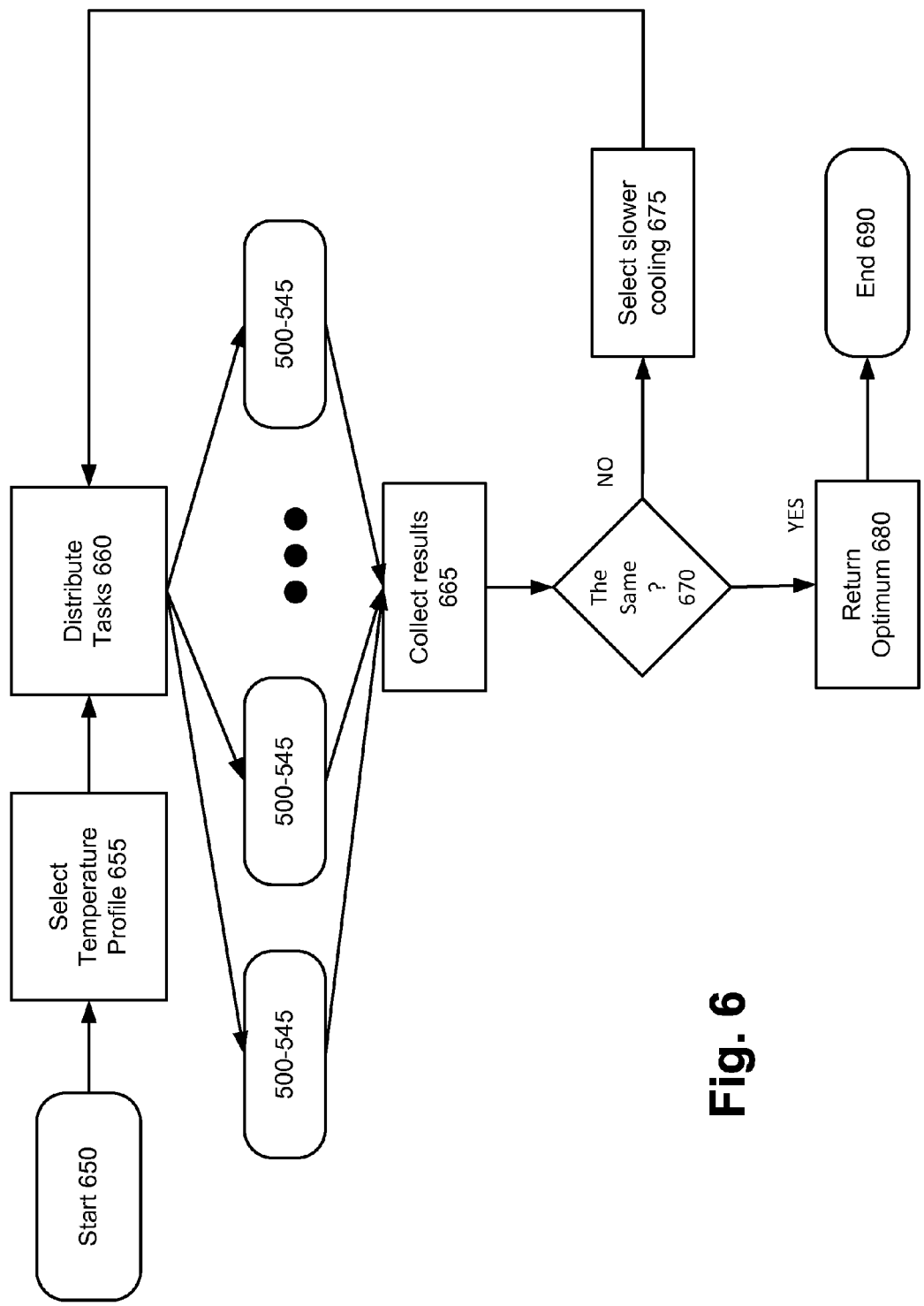
FIG. 6 is a flow chart illustrating a sequence of validation of a simulated annealing solution to the optimization algorithm incorporating the sequence of steps illustrated in FIG. 5.

With reference to FIG. 6, it is advantageous to verify that the state chosen by the simulated annealing at step 545 is the optimal choice. It has been found that the confidence in the optimality of the chosen state can be increased by performing multiple trials of the sequence illustrated in FIG. 5 (steps 500-545). The validation of the simulated annealing solution includes choosing a "temperature cooling" profile at step 655 and running multiple tasks for this "temperature profile." These tasks are distributed in step 660 and the results are collected at step 665. If results collected based on multiple runs are substantially the same, as determined at step 670, then the confidence is high that the optimal choice has been returned, 680, and the algorithm ends at step 690. If the results from multiple runs differ, based on comparison carried out at step 670, then "select slower cooling" profile is engaged at step 675. The operation of evaluating the tasks described in reference to steps 660-670 is repeated until the cohort of solutions converges based on comparison performed at step 670.

The choice of wavelength(s) and the weighting functions (or constraint parameters) representing partial or full operational cost of employing the device and used in the evaluation may include finite or discrete variables and continuous variables. The random perturbation of the wavelengths in the solution state can be augmented by a number of techniques, including those known in the art but not limited to gradient decent (i.e., if a change improved the result last time, make a further change in the same direction) and statistical sampling.

Convex optimization, as described by Stephen Boyd and Lieven Vandenberghe, (in *Convex Optimization*, Cambridge University Press; Mar. 8, 2004) and linear programming as described by R. Fletcher (in *Practical Methods of Optimization*, Wiley, 1987) are two additional techniques that can be used to find improved solutions to the quantified problem as stated above.

While the invention has been described through the above-presented examples of embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above.

For example, an implementation of a method of the invention may include a method for selecting a regime of operation of a spectrometric system (which contains a light source and which is configured to measure at least one material characteristic of at least one molecular analyte in a sample). Such method may include the steps of: (i) receiving data at an input, the data representing a material characteristic of said at least one analyte; (ii) defining a system of equations representing the at least one material characteristic of said at least one molecular analyte as a function of a determined optical path of light from the light source through the sample and one or more of (a) an attenuation coefficient of the sample, (b) an anisotropy characteristic of the sample and (c) an index of refraction of the sample associated with said light. The method additionally includes determining a solution of the system equation to define at least one operational wavelength at which a difference between a value of the material characteristic represented by said equation and the received data representing said material characteristic at the at least one operational wavelength is maximized. The step of defining a set of equations includes defining a matrix equation including a matrix-coefficient representing a cost-factor that includes one or more of a cost of manufacture of the light source that operates at the at least one operational wavelength an error associated with determination of the optical path, and a figure of merit associated with operational noise of the light source at said at least one operational wavelength. At least one molecular analyte may include two analytes, and the step of solving the equation may include solving a matrix equation to determine two operational wavelengths one of which is shorter than an isosbestic wavelength corresponding to said two analytes and another is longer than said isosbestic wavelength. Alternatively or in addition, the step of solving the equation may include solving a matrix equation to determine an operational wavelength which substantially coincides with an isosbestic wavelength of the two analytes.

In another modification, corresponding to a related embodiment, an apparatus is provided for measuring one or more properties of one or more molecular analytes of a sample. The apparatus includes a transmitter configured to emit a wave characterized by least one wavelength towards the sample; a receiver device configured to receive said wave that has interacted with the sample; and a processor in operable communication with the receiver and programmed to determine said one or more properties by solving a system of equations representing said one or more properties as functions of one or more of an optical path, an attenuation coefficient, a scattering coefficient, and an index of refraction of the one or more molecular analytes of the sample based at least on data representing the received wave.

In yet another related embodiment, a system for choosing a wavelength of operation of a spectrometric device is enabled. Such system includes (i) a tangible storage medium containing first data representing empirically-defined spectrally-dependent characteristic of at least first and second material components of a sample; (ii) a microprocessor in operable communication with the tangible storage medium, the microprocessor being configured to receive an input associated with an identification of the at least first and second material components of the sample; and (iii) a tangible non-transitory computer-readable medium on which are stored computer instructions. When the instructions are executed by the microprocessor, they cause the microprocessor to receive, from the tangible storage medium, the first data; and to solve a system of equations representing the empirically-defined spectrally dependent characteristic as functions of at least respectively corresponding concentrations of the at least first and second material components in the sample, spectrally-dependent paths of electromagnetic waves (EMWs) propagating through the sample, and at least one parameter representing operational utility of the spectrometric device. In determining the solution, the EMWs are considered to respectively correspond to the at least first sand second material components. As a result of solving the system of equation, wavelengths of operation of the spectrometric device are determined at which a figure of merit (which represents operational cost of employing the spectrometric device) is at least locally optimized. The system may additionally contain a display device adapted to generate a visually-perceivable representation of the empirically-defined spectrally-dependent characteristic and parameters representing the determined wavelengths of operation. The material components of the sample may include a confounding material component of the sample.

Accordingly, the invention should not be viewed as being limited to the disclosed embodiment(s).

What is claimed is:

1. A method for determining a spectral regime of operation of a spectrometric device that is cooperated with a sample, the device enabled to generate optical waves and configured to measure a property of a material component of the sample, the method comprising:

receiving at a user-input device, optical data obtained with light from a set of light sources of said spectrometric device and representing spectrally-dependent characteristics of M material components of the sample to be measured with the spectrometric device having at least one optical detector, M being greater than 1;

forming a first system of equations that expresses the optical data as functions of at least
   i) respectively corresponding concentrations of the M material components in the sample and
   ii) spectrally-dependent paths of optical waves through the sample, the optical waves respectively corresponding to the M material components;

forming a second system of equations including the first system of equations and additional equations employing at least one parameter representing operational utility of the device; and solving said second system of equations, with a programmable processor, to calculate such N wavelengths of operation of the device that a spectrally-dependent figure of merit is locally optimized at the wavelengths of operation, wherein to solve said second system of equations a number N of calculated wavelengths of operation smaller than the number M of the material components is required, and wherein said spectrally-dependent figure of merit includes propagation of variance, and transforming said set of light sources by replacing at least one light source from said set to form a transformed set of light sources that generate light at said N of calculated wavelengths.

2. A method according to claim 1, wherein said receiving includes receiving optical data representing, for each of the M material components, two or more of an attenuation coefficient, a scattering coefficient, a coefficient of anisotropy, a fluorescence parameter, an index of refraction, and a parameter representing a quantum response of the M material components to impinging optical waves.

3. A method according to claim 2, wherein said attenuation coefficient includes a molar attenuation coefficient.

4. A method according to claim 1, wherein said M material components include two or more of molecular analytes, cells, protein, hemoglobin, glucose, lipids, chromophore, hyperpolarized gas, carbon dioxide, carbon monoxide, and oxygen, and water.

5. A method according to claim 1, wherein said receiving includes receiving optical data that represent spectrally-dependent light scattering properties of each of the M material components of the sample.

6. A method according to claim 1, wherein said receiving includes receiving optical data representing spectral dependences of a chosen characteristic of each of the M material components of a sample that contains blood, at least the M material components including blood analyte.

7. A method according to claim 1, wherein said receiving includes acquiring, with the at least one optical detector, pulses of said optical waves transmitted in a defined sequence and correlating a sequence of acquired pulses with a sequence of transmitted pulses.

8. A method according to claim 1, wherein said forming of a second system of equations includes forming a matrix equation that includes a matrix coefficient representing one or more of
   i) a cost of manufacture of the device that operates at a wavelength of operation from the N wavelengths of operation,
   ii) an error associated with determination of said paths of optical waves, and
   iii) a figure of merit associated with operational noise of the device at said wavelength of operation.

9. A method according to claim 8, wherein said forming of a second system of equations includes forming a matrix equation that includes a matrix coefficient representing a figure of merit associated with operational noise of the device, which operational noise is calculated as a function of a change in light scattering of the M components as a wavelength of the optical waves is varied.

10. A method according to claim 1, wherein said solving includes optimizing the figure of merit that further includes at least one of a parameter representing manufacturing cost of the device, a parameter representing a size of the device, and a parameter representing power consumption of the device.

11. A method according to claim 1, wherein said solving includes solving the second system of equations to determine first and second wavelengths of operation one of which is shorter that an isosbestic wavelength corresponding to said M material components and another is longer than said isosbestic wavelength.

12. A method according to claim 1, wherein said solving includes employing an iterative algorithm comprising at least one of a simulated annealing algorithm, a gradient descent algorithm, and a linear programming algorithm.

13. A method according to claim 1, wherein said forming of a first system of equations includes defining a first system of equations representing said spectrally-dependent characteristics as a functions of respectively-corresponding concentrations parameters representing said material components in the sample, wherein said concentrations parameters include at least two of a cell count, a protein count, a hemoglobin level, a glucose level, a lipid level, percent of a chromophore, a gas concentration; a carbon dioxide concentration, an oxygen concentration a percent content of water, and a pH level.

14. A method according to claim 1, wherein said spectrally-dependent figure of merit represents operational cost of employing the device.

15. A method according to claim 1, wherein said spectrally-dependent figure of merit further represents a number of said at least one optical detector and a parameter of placement of said at least one optical detector with respect to the sample.

16. An apparatus for determining a spectral regime of operation of a spectrometric device, the system comprising:
a tangible storage medium containing optical data representing spectrally-dependent characteristics of M material components of a sample to be measured with the spectrometric device having at least one optical detector, M being greater than 1;
a microprocessor in operable communication with the tangible storage medium, the microprocessor being configured to receive an input associated with an identification of M material components of the sample; and
a tangible non-transitory computer-readable medium on which are stored computer instructions that, when the instructions are executed by the microprocessor, cause the microprocessor to:
receive, from the tangible storage medium, said optical data;
form a first system of equations that expresses said optical data as functions of at least
i) respectively corresponding concentrations of the M material components in the sample and
ii) spectrally-dependent paths of optical waves through the sample, the optical waves respectively corresponding to the M material components;
form a second system of equations including the first system of equations and additional equations employing at least one parameter representing operational utility of the device; and
solve said second system of equations with a programmable processor, to calculate such N wavelengths of operation of the device that a spectrally-dependent figure of merit is locally optimized at the wavelengths of operation, wherein to solve said second system of equations a number N of calculated wavelengths of operation smaller than the number M of the material components is required, and wherein said spectrally-dependent figure of merit includes propagation of variance, and
a set of light sources configured to generate light at a first set of predetermined wavelengths and in optical communication with the at least one optical detector, at least one light source from said set configured to be replaced, as a result of a calculation of said N wavelengths of operation of the device, with an auxiliary light source to form a modified set of light sources that is configured to generate light at a second set of predetermined wavelengths and in said optical communication, the second set of predetermined wavelengths including said N wavelengths of operation, the second set of predetermined wavelengths being different from the first set of predetermined wavelengths.

17. An apparatus according to claim 16, further comprising a display device cooperated with the microprocessor and adapted to generate a visually-perceivable representation of said spectrally-dependent characteristics and parameters representing the determined wavelengths of operation.

18. An apparatus according to claim 16, wherein the M material components of the sample include a confounding material component of the sample.

19. An apparatus according to claim 16, wherein the spectrometric device includes at least one source of optical waves that is operable least one wavelength from the determined wavelengths of operation.

20. An apparatus according to claim 16, wherein the spectrometric device includes an oximeter.

21. An apparatus according to claim 16, wherein said spectrally-dependent figure of merit further represents operational cost of employing the device.

22. An apparatus according to claim 16, wherein said optical data representing spectrally-dependent light-scattering properties of each of the M material components.

23. An apparatus according to claim 16, wherein said spectrally-dependent figure of merit further represents a number of said at least one optical detector and a parameter of placement of said at least one optical detector with respect to the sample.

24. A spectrometric system for measuring a property of a sample, the system comprising:
at least one source of optical radiation enabled to generate the optical radiation at least one wavelength of operation from a set of N pre-calculated wavelengths of operation;
at least one optical detector of the optical radiation in operable communication with the at least one source;
a supporting structure adapted to juxtapose the at least one source and the at least one optical detector with the sample, the sample characterized by M material components having respective M spectrally-dependent characteristics;
a data-processing unit cooperated with the source and the at least one optical detector and configured to quantify optical radiation received by the at least one optical detector from the source through the sample and to generate output data representing such quantification,
wherein the output data includes said N pre-calculated wavelengths of operation and a spectrally-dependent figure of merit of operation of the spectrometric system,
wherein N is smaller than M,
wherein the spectrally-dependent figure of merit includes propagation of variance;
and
a data-output device operable to present the output data in a user-defined format.

25. A system according to claim 24 that includes a pulse oximeter and wherein the M spectrally-dependent characteristics of the M material components of the sample include a light scattering characteristic.

26. A system according to claim 24, wherein the set of N pre-calculated wavelengths of operation is defined by solving a system of equations that includes equations representing the spectrally dependent characteristics as a function of respectively-corresponding concentrations of the M material components of the sample, wherein said concentrations include at least one of a cell count, a protein count, a hemoglobin level, a glucose level, a lipid level, percent of a chromophore in the sample, a gas concentration; a percent water, and a pH level.

27. A system according to claim 26, wherein the gas concentration includes at least one of a carbon dioxide concentration and an oxygen concentration, and wherein the A material components include hemoglobin.

28. A system according to claim 24, wherein said spectrally-dependent figure of merit further represents operation cost of employing the system.

29. A system according to claim 24, wherein said optical data representing spectrally-dependent light-scattering properties of each of the M material components.

30. A system according to claim 24, wherein said spectrally-dependent figure of merit further represents a number of said at least one optical detector and a parameter of placement of said at least one optical detector with respect to the sample.

\* \* \* \* \*

UNITED STATES PATENT AND TRADEMARK OFFICE
CERTIFICATE OF CORRECTION

PATENT NO. : 9,714,900 B2  
APPLICATION NO. : 14/397810  
DATED : July 25, 2017  
INVENTOR(S) : Clifton R Haider et al.

Page 1 of 1

It is certified that error appears in the above-identified patent and that said Letters Patent is hereby corrected as shown below:

In the Specification

Column 11, Line 24, "(S)" should be --($\delta$)--.

Column 15, Line 54, "$\phi(0\leq\phi\leq \pi)$" should be --($\varphi$ $(0\leq\varphi\leq \pi)$--.

In the Claims

Column 30, Claim 19, Line 18, "operable least" should be --operable at at least--.

Column 31, Claim 27, Line 11, "A" should be --M--.

Signed and Sealed this  
Twenty-eighth Day of November, 2017

Joseph Matal  
*Performing the Functions and Duties of the*  
*Under Secretary of Commerce for Intellectual Property and*  
*Director of the United States Patent and Trademark Office*